(12) United States Patent
Konstorum et al.

(10) Patent No.: US 11,266,303 B2
(45) Date of Patent: Mar. 8, 2022

(54) OBLONG ENDOSCOPE SHEATH

(71) Applicant: GYRUS ACMI, INC., Southborough, MA (US)

(72) Inventors: Gregory S. Konstorum, Stamford, CT (US); Ming J. Cheng, W. Warwick, RI (US); Daniel R. Goldberg, Memphis, TN (US)

(73) Assignee: Gyrus Acmi, Inc., Westborough, MA (US)

( * ) Notice: Subject to any disclaimer, the term of this patent is extended or adjusted under 35 U.S.C. 154(b) by 123 days.

(21) Appl. No.: 16/580,079

(22) Filed: Sep. 24, 2019

(65) Prior Publication Data

US 2020/0015665 A1    Jan. 16, 2020

Related U.S. Application Data

(62) Division of application No. 15/917,212, filed on Mar. 9, 2018, now Pat. No. 10,478,052, which is a division
(Continued)

(51) Int. Cl.
| | |
|---|---|
| *A61B 1/015* | (2006.01) |
| *A61B 1/00* | (2006.01) |
| *A61B 90/70* | (2016.01) |
| *A61B 1/06* | (2006.01) |
| *A61B 1/12* | (2006.01) |

(52) U.S. Cl.
CPC .......... *A61B 1/015* (2013.01); *A61B 1/00068* (2013.01); *A61B 1/00119* (2013.01); *A61B 1/00135* (2013.01); *A61B 1/00142* (2013.01); *A61B 1/06* (2013.01); *A61B 1/126* (2013.01);
(Continued)

(58) Field of Classification Search
CPC . A61B 1/015; A61B 1/00068; A61B 1/00119; A61B 1/00135; A61B 1/00147; A61B 1/06; A61B 1/126; A61B 90/70
See application file for complete search history.

(56) References Cited

U.S. PATENT DOCUMENTS 939,034 A * 11/1909 Kolb .................. A61B 1/00195
600/163
1,555,003 A    9/1925 Greenberg
(Continued)

FOREIGN PATENT DOCUMENTS

| CN | 1719997 A | 1/2006 |
|---|---|---|
| CN | 101188966 A | 5/2008 |

(Continued)

OTHER PUBLICATIONS

US 5,772,579 A, 06/1998, Reisdorf (withdrawn)
(Continued)

*Primary Examiner* — Alexandra L Newton
*Assistant Examiner* — Jae Woo
(74) *Attorney, Agent, or Firm* — Schwegman Lundberg & Woessner, P.A.

(57) ABSTRACT

An endoscope sheath configured to receive a portion of an endoscope can include a tubular member and a positioning device located on the tubular member. The positioning device can include a crimp that is configured to prevent distal movement of a portion of the endoscope relative to the tubular member.

17 Claims, 13 Drawing Sheets

Related U.S. Application Data of application No. 14/496,473, filed on Sep. 25, 2014, now Pat. No. 10,028,644.

(60) Provisional application No. 61/882,652, filed on Sep. 26, 2013.

(52) U.S. Cl.
CPC .......... *A61B 90/70* (2016.02); *A61B 1/00128* (2013.01); *A61B 2090/701* (2016.02)

(56) References Cited

U.S. PATENT DOCUMENTS

| | | | |
|---|---|---|---|
| 2,112,056 A * | 3/1938 | Wappler | A61B 1/12 600/153 |
| 3,071,129 A | 1/1963 | Wasserman | |
| 3,321,265 A | 5/1967 | Clave et al. | |
| 3,572,325 A | 3/1971 | Bazell et al. | |
| 3,592,199 A | 7/1971 | Ostensen et al. | |
| 3,604,582 A * | 9/1971 | Boudin | B65D 50/06 215/202 |
| 3,610,478 A | 10/1971 | Johnston | |
| 3,659,423 A | 5/1972 | Lair et al. | |
| 3,675,641 A | 7/1972 | Fiore | |
| 3,689,083 A | 9/1972 | Greenawalt | |
| 3,699,504 A * | 10/1972 | Huber | H01R 9/0518 439/585 |
| 3,903,877 A | 9/1975 | Terada | |
| 3,969,824 A | 7/1976 | Widen et al. | |
| 4,254,762 A | 3/1981 | Yoon | |
| 4,281,646 A | 8/1981 | Kinoshita | |
| 4,312,375 A | 1/1982 | Leinemann | |
| 4,525,220 A | 6/1985 | Sasa et al. | |
| 4,548,197 A | 10/1985 | Kinoshita | |
| 4,579,597 A | 4/1986 | Sasa et al. | |
| 4,593,682 A | 6/1986 | Heckele | |
| 4,646,722 A | 3/1987 | Silverstein et al. | |
| 4,659,328 A * | 4/1987 | Potter | A61M 25/09025 600/434 |
| 4,667,656 A | 5/1987 | Yabe | |
| 4,756,303 A | 7/1988 | Kawashima et al. | |
| 4,813,455 A * | 3/1989 | Iqbal | F16K 31/60 137/625.17 |
| 4,850,342 A | 7/1989 | Hashiguchi | |
| 4,907,395 A | 3/1990 | Opie et al. | |
| 4,991,565 A | 2/1991 | Takahashi | |
| 5,025,778 A * | 6/1991 | Silverstein | A61B 1/00078 600/104 |
| 5,027,792 A | 7/1991 | Meyer | |
| 5,050,585 A | 9/1991 | Takahashi | |
| 5,102,344 A * | 4/1992 | Tadokoro | H01R 23/26 439/98 |
| 5,167,220 A | 12/1992 | Brown | |
| 5,170,774 A | 12/1992 | Heckele | |
| 5,176,645 A | 1/1993 | Guerrero | |
| 5,178,606 A | 1/1993 | Ognier et al. | |
| 5,181,267 A * | 1/1993 | Gerace | G02B 6/3847 385/80 |
| 5,199,417 A | 4/1993 | Muller et al. | |
| 5,207,213 A | 5/1993 | Auhll et al. | |
| 5,225,001 A | 7/1993 | Manni et al. | |
| 5,237,984 A | 8/1993 | Williams et al. | |
| 5,261,889 A | 11/1993 | Laine et al. | |
| 5,269,756 A | 12/1993 | Dryden | |
| 5,313,934 A | 5/1994 | Wiita et al. | |
| 5,328,458 A | 7/1994 | Sekino et al. | |
| 5,354,267 A | 10/1994 | Niermann et al. | |
| 5,362,251 A * | 11/1994 | Bielak | H01R 9/053 439/394 |
| 5,377,668 A | 1/1995 | Ehmsen et al. | |
| 5,386,817 A | 2/1995 | Jones | |
| 5,408,991 A | 4/1995 | Iida et al. | |
| 5,413,092 A | 5/1995 | Williams, III et al. | |
| 5,419,309 A | 5/1995 | Biehl | |
| 5,419,310 A | 5/1995 | Frassica et al. | |
| 5,439,022 A | 8/1995 | Summers et al. | |
| 5,447,148 A | 9/1995 | Oneda et al. | |
| 5,486,155 A | 1/1996 | Muller et al. | |
| 5,505,707 A | 4/1996 | Manzie et al. | |
| 5,509,892 A * | 4/1996 | Bonnet | A61B 1/00094 600/129 |
| 5,514,074 A | 5/1996 | Yabe et al. | |
| 5,518,501 A | 5/1996 | Oneda et al. | |
| 5,522,874 A * | 6/1996 | Gates | A61N 1/0575 607/120 |
| 5,522,875 A * | 6/1996 | Gates | A61N 1/056 600/585 |
| 5,536,234 A * | 7/1996 | Newman | A61B 1/00091 600/104 |
| 5,551,448 A | 9/1996 | Matula et al. | |
| 5,554,100 A | 9/1996 | Leiner | |
| 5,554,112 A | 9/1996 | Walbrink et al. | |
| 5,556,258 A | 9/1996 | Lange et al. | |
| 5,575,756 A | 11/1996 | Karasawa et al. | |
| 5,593,404 A * | 1/1997 | Costello | A61B 18/24 600/105 |
| 5,630,795 A | 5/1997 | Kuramoto et al. | |
| 5,647,840 A | 7/1997 | D'Amelio | |
| 5,662,588 A | 9/1997 | Iida | |
| 5,681,262 A | 10/1997 | Isse | |
| 5,685,823 A | 11/1997 | Ito et al. | |
| 5,690,605 A | 11/1997 | Hamlin et al. | |
| 5,695,448 A | 12/1997 | Kimura et al. | |
| 5,697,888 A | 12/1997 | Kobayashi et al. | |
| 5,700,236 A | 12/1997 | Sauer | |
| 5,702,348 A | 12/1997 | Harhen | |
| 5,733,245 A | 3/1998 | Kawano | |
| 5,735,792 A | 4/1998 | Vanden Hoek et al. | |
| 5,779,625 A * | 7/1998 | Suzuki | A61B 1/00057 600/121 |
| 5,785,689 A * | 7/1998 | de Toledo | A61B 17/3478 604/158 |
| 5,792,045 A | 8/1998 | Adair | |
| 5,797,836 A | 8/1998 | Lucey et al. | |
| 5,823,940 A | 10/1998 | Newman | |
| 5,944,654 A | 8/1999 | Crawford | |
| 5,989,183 A | 11/1999 | Reisdorf et al. | |
| 6,110,103 A | 4/2000 | Donofrio | |
| 6,126,592 A | 10/2000 | Proch et al. | |
| 6,181,442 B1 | 1/2001 | Ogura et al. | |
| 6,196,967 B1 | 3/2001 | Lim | |
| 6,282,442 B1 | 8/2001 | DeStefano et al. | |
| 6,340,344 B1 | 1/2002 | Christopher | |
| 6,354,813 B1 | 3/2002 | Laing | |
| 6,447,446 B1 | 9/2002 | Smith et al. | |
| 6,478,731 B2 | 11/2002 | Speier et al. | |
| 6,558,379 B1 | 5/2003 | Batchelor et al. | |
| 6,645,140 B2 * | 11/2003 | Brommersma | A61B 1/12 600/105 |
| 6,652,484 B1 | 11/2003 | Hunckler et al. | |
| 6,824,544 B2 | 11/2004 | Boebel et al. | |
| 6,911,005 B2 | 6/2005 | Ouchi et al. | |
| 7,160,247 B2 | 1/2007 | Deppmeier | |
| 7,192,396 B2 | 3/2007 | Boulais | |
| 7,252,110 B2 | 8/2007 | Semeia | |
| 7,270,647 B2 | 9/2007 | Karpowicz et al. | |
| 7,413,542 B2 | 8/2008 | Kucklick et al. | |
| 7,708,689 B2 | 5/2010 | Deppmeier et al. | |
| 7,736,301 B1 | 6/2010 | Webler et al. | |
| 7,758,497 B2 | 7/2010 | Hem | |
| 7,766,819 B2 | 8/2010 | Matsumoto | |
| 7,811,228 B2 | 10/2010 | Adams | |
| 7,942,814 B2 | 5/2011 | Remijan et al. | |
| 8,001,984 B2 | 8/2011 | Sasaki | |
| 8,029,438 B2 | 10/2011 | Hagihara | |
| 8,047,215 B1 | 11/2011 | Sasaki | |
| 8,066,660 B2 | 11/2011 | Gregersen et al. | |
| 8,079,952 B2 | 12/2011 | Fujimoto | |
| 8,092,415 B2 | 1/2012 | Moehle et al. | |
| 8,148,635 B1 * | 4/2012 | Gretz | H02G 3/123 174/50 |
| 8,231,574 B2 | 7/2012 | Haack et al. | |

(56) References Cited

U.S. PATENT DOCUMENTS

| | | | |
|---|---|---|---|
| 8,231,658 B2 | 7/2012 | Oskin et al. | |
| 8,337,470 B2 | 12/2012 | Prasad et al. | |
| 8,393,328 B2 | 3/2013 | Angel | |
| 8,394,013 B2 | 3/2013 | Ichimura | |
| 8,409,109 B2 | 4/2013 | Tiesma | |
| 8,419,624 B2 | 4/2013 | James et al. | |
| 8,663,090 B2 | 3/2014 | Fujimoto | |
| 8,870,752 B2 | 10/2014 | Avitsian et al. | |
| 8,888,689 B2 | 11/2014 | Poll et al. | |
| 8,911,415 B2 | 12/2014 | Knapp | |
| 8,915,842 B2 | 12/2014 | Weisenburgh, II et al. | |
| 8,978,657 B2 | 3/2015 | Sandmore et al. | |
| 9,078,562 B2 | 7/2015 | Poll et al. | |
| 9,078,781 B2 * | 7/2015 | Ryan | A61F 2/958 |
| 9,144,664 B2 | 9/2015 | Jacobsen et al. | |
| 9,155,453 B2 | 10/2015 | Kumar | |
| 9,332,894 B2 | 5/2016 | Cheng et al. | |
| 9,795,765 B2 * | 10/2017 | Romoscanu | A61M 25/0053 |
| 10,022,040 B2 | 7/2018 | Cheng et al. | |
| 10,028,644 B2 | 7/2018 | Konstorum et al. | |
| 10,098,524 B2 | 10/2018 | Cheng et al. | |
| 10,478,052 B2 | 11/2019 | Konstorum et al. | |
| 10,631,717 B2 | 4/2020 | Cheng et al. | |
| 10,716,736 B2 * | 7/2020 | Schuldt-Lieb | A61J 1/1406 |
| 10,799,097 B2 | 10/2020 | Cheng et al. | |
| 2001/0000041 A1 | 3/2001 | Seimon | |
| 2001/0011162 A1 | 8/2001 | Epstein | |
| 2002/0120180 A1 | 8/2002 | Speier et al. | |
| 2002/0166946 A1 | 11/2002 | Iizuka et al. | |
| 2003/0130565 A1 * | 7/2003 | Muller | A61B 1/00135 600/156 |
| 2004/0073088 A1 | 4/2004 | Friedman et al. | |
| 2005/0025646 A1 | 2/2005 | Miller et al. | |
| 2005/0085694 A1 | 4/2005 | Nakao | |
| 2005/0171470 A1 | 8/2005 | Kucklick et al. | |
| 2005/0197531 A1 | 9/2005 | Cabiri et al. | |
| 2005/0267330 A1 | 12/2005 | Deppmeier | |
| 2006/0007427 A1 | 1/2006 | Sekiya et al. | |
| 2006/0020165 A1 * | 1/2006 | Adams | A61B 1/00094 600/121 |
| 2006/0041186 A1 * | 2/2006 | Vancaillie | A61B 1/00135 600/128 |
| 2006/0069306 A1 | 3/2006 | Banik et al. | |
| 2006/0074274 A1 | 4/2006 | Friedman et al. | |
| 2006/0199998 A1 | 9/2006 | Akui et al. | |
| 2006/0200047 A1 * | 9/2006 | Galdonik | A61M 25/0138 600/585 |
| 2006/0211916 A1 | 9/2006 | Kasahara et al. | |
| 2006/0258906 A1 | 11/2006 | Binmoeller | |
| 2006/0264995 A1 | 11/2006 | Fanton et al. | |
| 2006/0276688 A1 | 12/2006 | Surti | |
| 2007/0106113 A1 | 5/2007 | Ravo | |
| 2007/0112314 A1 * | 5/2007 | Harding | A61M 39/02 604/247 |
| 2007/0138206 A1 | 6/2007 | Yamamoto et al. | |
| 2007/0213668 A1 | 9/2007 | Spitz | |
| 2007/0250150 A1 * | 10/2007 | Pal | A61M 25/0097 604/538 |
| 2007/0270646 A1 | 11/2007 | Weiner | |
| 2007/0270788 A1 | 11/2007 | Nahen et al. | |
| 2008/0021279 A1 | 1/2008 | Takahashi | |
| 2008/0028831 A1 * | 2/2008 | Nakashima | G01N 27/4077 73/31.05 |
| 2008/0045859 A1 | 2/2008 | Fritsch | |
| 2008/0067066 A1 * | 3/2008 | Okumura | G01N 27/4077 204/424 |
| 2008/0072970 A1 | 3/2008 | Gasser et al. | |
| 2008/0081948 A1 | 4/2008 | Weisenburgh et al. | |
| 2008/0091074 A1 | 4/2008 | Kumar et al. | |
| 2008/0124972 A1 * | 5/2008 | Kobayashi | H01R 9/0518 439/585 |
| 2008/0146873 A1 * | 6/2008 | Adams | A61B 17/42 600/104 |
| 2008/0200764 A1 | 8/2008 | Okada | |
| 2008/0242935 A1 | 10/2008 | Inoue | |
| 2008/0255424 A1 | 10/2008 | Durgin et al. | |
| 2008/0262308 A1 | 10/2008 | Prestezog | |
| 2009/0005643 A1 | 1/2009 | Smith et al. | |
| 2009/0198105 A1 | 8/2009 | Sugisawa | |
| 2009/0205189 A1 | 8/2009 | Nimkar et al. | |
| 2009/0234193 A1 | 9/2009 | Weisenburgh, II et al. | |
| 2009/0244223 A1 | 10/2009 | Mizutani et al. | |
| 2010/0010299 A1 * | 1/2010 | Bakos | A61B 1/005 600/108 |
| 2010/0016786 A1 | 1/2010 | Modesitt et al. | |
| 2010/0019786 A1 | 1/2010 | Potok et al. | |
| 2010/0081878 A1 | 4/2010 | Byers et al. | |
| 2010/0120302 A1 * | 5/2010 | Kumakura | H01R 4/185 439/878 |
| 2010/0198012 A1 * | 8/2010 | Poole | A61B 1/00142 600/115 |
| 2010/0198014 A1 | 8/2010 | Poll et al. | |
| 2011/0208001 A1 | 8/2011 | Haeckl et al. | |
| 2011/0230716 A1 | 9/2011 | Fujimoto | |
| 2011/0230717 A1 | 9/2011 | Konstorum et al. | |
| 2011/0295066 A1 | 12/2011 | Fan | |
| 2012/0065569 A1 | 3/2012 | Steegers et al. | |
| 2012/0178995 A1 | 7/2012 | Newton, IV | |
| 2012/0309240 A1 * | 12/2012 | Yang | H01R 13/14 439/843 |
| 2012/0316394 A1 | 12/2012 | Yoshida et al. | |
| 2013/0183002 A1 * | 7/2013 | Maesoba | G02B 6/3877 385/72 |
| 2013/0205936 A1 | 8/2013 | Schmieding et al. | |
| 2013/0211433 A1 | 8/2013 | Kadykowski et al. | |
| 2013/0216186 A1 * | 8/2013 | Ott | G02B 6/3863 385/70 |
| 2013/0217970 A1 | 8/2013 | Weisenburgh, II | |
| 2013/0267777 A1 | 10/2013 | Avitsian et al. | |
| 2013/0289595 A1 | 10/2013 | Edwards et al. | |
| 2014/0163360 A1 | 6/2014 | Stevens-Wright et al. | |
| 2014/0364871 A1 | 12/2014 | Kucklick | |
| 2014/0379064 A1 * | 12/2014 | Pacetti | A61F 2/82 623/1.11 |
| 2015/0045678 A1 | 2/2015 | Ohzawa | |
| 2015/0087906 A1 | 3/2015 | Kucklick et al. | |
| 2015/0087907 A1 | 3/2015 | Konstorum et al. | |
| 2015/0087908 A1 | 3/2015 | Cheng et al. | |
| 2015/0087909 A1 | 3/2015 | Cheng et al. | |
| 2015/0087911 A1 | 3/2015 | Konstorum et al. | |
| 2015/0182108 A1 | 7/2015 | Fukuda | |
| 2015/0257633 A1 | 9/2015 | Hassidov et al. | |
| 2015/0267996 A1 * | 9/2015 | Su | F41F 3/052 89/1.816 |
| 2015/0282695 A1 | 10/2015 | Tay | |
| 2016/0089006 A1 | 3/2016 | Poll | |
| 2016/0093984 A1 * | 3/2016 | Iwamoto | H01R 9/035 439/607.55 |
| 2016/0095510 A1 | 4/2016 | Oskin | |
| 2016/0220100 A1 | 8/2016 | Cheng et al. | |
| 2017/0049514 A1 * | 2/2017 | Cosman | A61M 25/0662 |
| 2017/0224197 A1 * | 8/2017 | Green | A61B 1/015 |
| 2018/0192858 A1 | 7/2018 | Konstorum et al. | |
| 2018/0242962 A1 * | 8/2018 | Walen | A61B 17/1631 |
| 2018/0279861 A1 | 10/2018 | Cheng et al. | |
| 2018/0353057 A1 | 12/2018 | Cheng et al. | |
| 2019/0312388 A1 * | 10/2019 | Maesoba | H01R 13/6585 |
| 2020/0046213 A1 * | 2/2020 | Bendory | A61B 1/0669 |

FOREIGN PATENT DOCUMENTS

| | | |
|---|---|---|
| CN | 102149312 A | 8/2011 |
| CN | 102348404 A | 2/2012 |
| CN | 102813496 A | 12/2012 |
| CN | 105491935 A | 4/2016 |
| CN | 105491938 A | 4/2016 |
| CN | 105491938 B | 11/2018 |
| CN | 105491935 B | 6/2019 |
| EP | 0374727 A1 | 6/1990 |
| EP | 1323381 A1 | 7/2003 |
| EP | 3016572 A1 | 5/2016 |
| EP | 3016574 A1 | 5/2016 |

(56) References Cited

FOREIGN PATENT DOCUMENTS

| | | |
|---|---|---|
| EP | 3016572 B1 | 12/2020 |
| EP | 3016574 B1 | 3/2021 |
| JP | S6218101 U | 2/1987 |
| JP | H05/038323 A | 2/1993 |
| JP | H06/189893 A | 7/1994 |
| JP | H07275185 A | 10/1995 |
| JP | H07/308286 | 11/1995 |
| JP | H0828173 A | 1/1996 |
| JP | H08/501720 A | 2/1996 |
| JP | H0817337 | 7/1996 |
| JP | H08243071 A | 9/1996 |
| JP | 2003167202 A | 6/2003 |
| JP | 2005/040184 A | 2/2005 |
| JP | 2007117289 A | 5/2007 |
| JP | 2008-28985 A | 12/2008 |
| JP | 2009-247797 A | 10/2009 |
| JP | 2012/045325 A | 3/2012 |
| JP | 2012523855 A | 10/2012 |
| JP | 2012254188 A | 12/2012 |
| JP | 2013169380 A | 9/2013 |
| JP | 2016529032 A | 9/2016 |
| JP | 2016529033 A | 9/2016 |
| JP | 6297156 B2 | 3/2018 |
| JP | 2018114296 A | 7/2018 |
| JP | 6526272 B2 | 5/2019 |
| JP | 2019166332 A | 10/2019 |
| WO | 2002/033296 A2 | 4/2002 |
| WO | 2012/069592 A1 | 5/2012 |
| WO | WO-2015047980 A1 | 4/2015 |
| WO | WO-2015047990 A1 | 4/2015 |
| WO | WO-2015048270 A1 | 4/2015 |
| WO | WO-2015048406 A1 | 4/2015 |

OTHER PUBLICATIONS

"U.S. Appl. No. 16/002,498, Corrected Notice of Allowability dated Aug. 27, 2020", 2 pgs.
"U.S. Appl. No. 16/002,498, Notice of Allowance dated Jun. 4, 2020", 7 pgs.
"European Application Serial No. 14777479.8, Communication Pursuant to Article 94(3) EPC dated Jun. 12, 2020", 4 pgs.
"European Application Serial No. 14777479.8, Response filed Sep. 10, 2020 to Communication Pursuant to Article 94(3) EPC dated Jun. 12, 2020", 4 pgs.
"Japanese Application Serial No. 2019-087875, Notification of Reasons for Rejection dated Jun. 16, 2020", w/ English Translation, 12 pgs.
"Japanese Application Serial No. 2019-087875, Office Action dated Jan. 5, 2021", with English translation, 6 pgs.
"Japanese Application Serial No. 2019-087875, Response filed Sep. 16, 2020 to Notification of Reasons for Rejection dated Jun. 16, 2020", w/ English Claims, 9 pgs.
U.S. Appl. No. 14/493,581, filed Sep. 23, 2014, Endoscope Sheath Deflection Devices.
U.S. Appl. No. 14/493,700, filed Sep. 23, 2014, Endoscope Sheath Arm, U.S. Pat. No. 10,098,524.
U.S. Appl. No. 16/106,390, filed Aug. 21, 2018, Endoscope Sheath Arm, U.S. Pat. No. 10,631,717.
U.S. Appl. No. 14/496,473, filed Sep. 25, 2014, Oblong Endoscope Sheath, U.S. Pat. No. 10,028,644.
U.S. Appl. No. 15/917,212, filed Mar. 9, 2018, Oblong Endoscope Sheath, U.S. Pat. No. 10,478,052.
U.S. Appl. No. 14/497,815, filed Sep. 26, 2014, Endoscope System Including a Resilient Reservoir, U.S. Pat. No. 9,332,894.
U.S. Appl. No. 15/095,651, filed Apr. 11, 2016, Endoscope System Including a Resilient Reservoir, U.S. Pat. No. 10,022,040.
U.S. Appl. No. 16/002,498, filed Jun. 7, 2018, Endoscope System Including a Resilient Reservoir.
Potentially Related Application, U.S. Appl. No. 14/497,815, dated Sep. 26, 2014.
Potentially Related Application, U.S. Appl. No. 14/493,581, dated Sep. 23, 2014.
Potentially Related Application, U.S. Appl. No. 14/493,700, dated Sep. 23, 2014.
Potentially Related Application, U.S. Appl. No. 14/551,208, dated Nov. 24, 2014.
Potentially Related Application, U.S. Appl. No. 14/551,440, dated Nov. 24, 2014.
State Intellectual Property Office of China Office Action for Application No. 201480047065.X, dated Feb. 28, 2017.
Japanese Office Action dated Jan. 31, 2017, for Application No. 2016-537952.
Japanese Office Action for Japanese Patent Application No. 2016-537952; dated Oct. 3, 2017.
Japanese Decision to Grant for Application No. 2016-537952, dated Jan. 23, 2018.
European Office Action, EP Application No. 14781019.6 dated Apr. 24, 2019.
Chinese Office Action from the State Intellectual Property Office for Application No. 20140047065 dated Sep. 11, 2018.
Chinese Office Action from the State Intellectual Property Office for Application No. 20140047065 dated Mar. 13, 2018.
Japanese Office Action, JP Application No. 2018-028128 dated Dec. 18, 2019.
"U.S. Appl. No. 14/493,581, Advisory Action dated Jan. 12, 2018", 3 pgs.
"U.S. Appl. No. 14/493,581, Advisory Action dated Apr. 26, 2017", 3 pgs.
"U.S. Appl. No. 14/493,581, Advisory Action dated Aug. 19, 2016", 3 pgs.
"U.S. Appl. No. 14/493,581, Applicant's Summary of Examiner Interview filed Sep. 26, 2016", 1 pg.
"U.S. Appl. No. 14/493,581, Examiner interview Summary dated Apr. 18, 2016", 3 pgs.
"U.S. Appl. No. 14/493,581, Examiner Interview Summary dated Aug. 24, 2016", 3 pgs.
"U.S. Appl. No. 14/493,581, Final Office Action dated Feb. 9, 2017", 11 pgs.
"U.S. Appl. No. 14/493,581, Final Office Action dated May 18, 2016", 10 pgs.
"U.S. Appl. No. 14/493,581, Final Office Action dated Oct. 19, 2017", 11 pgs.
"U.S. Appl. No. 14/493,581, Non Final Office Action dated Jan. 29, 2016", 13 pgs.
"U.S. Appl. No. 14/493,581, Non Final Office Action dated Jun. 29, 2017", 10 pgs.
"U.S. Appl. No. 14/493,581, Non Final Office Action dated Oct. 5, 2016", 9 pgs.
"U.S. Appl. No. 14/493,581, Response filed Apr. 3, 2017 to Final Office Action dated Feb. 9, 2017", 14 pgs.
"U.S. Appl. No. 14/493,581, Response filed Apr. 21, 2016 to Non Final Office Action dated Jan. 29, 2016", 14 pgs.
"U.S. Appl. No. 14/493,581, Response filed Jul. 13, 2016 to Final Office Action dated May 18, 2016", 10 pgs.
"U.S. Appl. No. 14/493,581, Response filed Sep. 13, 2017 to Non Final Office Action dated Jun. 29, 2017", 14 pgs.
"U.S. Appl. No. 14/493,581, Response filed Dec. 18, 2017 to Final Office Action dated Oct. 19, 2017", 15 pgs.
"U.S. Appl. No. 14/493,581, Response filed Dec. 29, 2016 to Non Final Office Action dated Oct. 5, 2016", 13 pgs.
"U.S. Appl. No. 14/493,700, 312 Amendment filed Aug. 21, 2018", 5 pgs.
"U.S. Appl. No. 14/493,700, Advisory Action dated Sep. 28, 2017", 3 pgs.
"U.S. Appl. No. 14/493,700, Advisory Action dated Nov. 17, 2016", 3 pgs.
"U.S. Appl. No. 14/493,700, Appeal Decision mailed Jul. 11, 2018", 2 pgs.
"U.S. Appl. No. 14/493,700, Examiner Interview Summary dated May 11, 2017", 4 pgs.
"U.S. Appl. No. 14/493,700, Examiner Interview Summary dated May 24, 2018", 4 pgs.

(56) References Cited

OTHER PUBLICATIONS

"U.S. Appl. No. 14/493,700, Examiner Interview Summary dated Jun. 27, 2016". 4 pgs.
"U.S. Appl. No. 14/493,700, Final Office Action dated Mar. 21, 2018", 9 pgs.
"U.S. Appl. No. 14/493,700, Final Office Action dated Jun. 15, 2017", 8 pgs.
"U.S. Appl. No. 14/493,700, Final Office Action dated Sep. 7, 2016", 12 pgs.
"U.S. Appl. No. 14/493,700, Non Final Office Action dated Feb. 3, 2017", 10 pgs.
"U.S. Appl. No. 14/493,700, Non Final Office Action dated Mar. 23, 2016", 12 pgs.
"U.S. Appl. No. 14/493,700, Non Final Office Action dated Nov. 16, 2017", 10 pgs.
"U.S. Appl. No. 14/493,700, Notice of Allowance dated Jul. 23, 2018", 7 pgs.
"U.S. Appl. No. 14/493,700, Pre-Appeal Brief filed Jun. 12, 2018", 5 pgs.
"U.S. Appl. No. 14/493,700, PTO Response to Rule 312 Communication dated Sep. 6, 2018", 2 pgs.
"U.S. Appl. No. 14/493,700, Response filed Feb. 15, 2018 to Non Final Office Action dated Nov. 16, 2017", 11 pgs.
"U.S. Appl. No. 14/493,700, Response filed May 3, 2017 to Non Final Ofice Action dated Feb. 3, 2017", 16 pgs.
"U.S. Appl. No. 14/493,700, Response filed Jun. 23, 2016 to Non Final Office Action dated Mar. 23, 2016", 16 pgs.
"U.S. Appl. No. 14/493,700, Response filed Aug. 15, 2017 to Final Office Action dated Jun. 15, 2017", 11 pgs.
"U.S. Appl. No. 14/493,700, Response filed Oct. 16, 2017 to Advisory Action dated Sep. 28, 2017", 16 pgs.
"U.S. Appl. No. 14/493,700, Response filed Nov. 7, 2016 to Final Office Action dated Sep. 7, 2016", 13 pgs.
"U.S. Appl. No. 14/496,473, 312 Amendment filed Jun. 12, 2018", 4 pgs.
"U.S. Appl. No. 14/496,473, Advisory Action dated Jul. 27, 2017", 3 pgs.
"U.S. Appl. No. 14/496,473, Advisory Action dated Dec. 7, 2016", 3 pgs.
"U.S. Appl. No. 14/496,473, Examiner Interview Summary dated May 3, 2017", 2 pgs.
"U.S. Appl. No. 14/496,473, Final Office Action dated May 11, 2017", 8 pgs.
"U.S. Appl. No. 14/496,473, Final Office Action dated Sep. 13, 2016", 7 pgs.
"U.S. Appl. No. 14/496,473, Final Office Action dated Dec. 29, 2017", 11 pgs.
"U.S. Appl. No. 14/496,473, Non Final Office Action dated Jan. 17, 2017", 9 pgs.
"U.S. Appl. No. 14/496,473, Non Final Office Action dated Apr. 22, 2016", 9 pgs.
"U.S. Appl. No. 14/496,473, Non Final Office Action dated Aug. 31, 2017", 7 pgs.
"U.S. Appl. No. 14/496,473, Notice of Allowance dated May 23, 2018", 8 pgs.
"U.S. Appl. No. 14/496,473, PTO Response to Rule 312 Communication dated Jun. 22, 2018", 2 pgs.
"U.S. Appl. No. 14/496,473, Response filed Feb. 15, 2018 to Final Office Action dated Dec. 29, 2017", 14 pgs.
"U.S. Appl. No. 14/496,473, Response filed Mar. 24, 2016 to Restriction Requirement dated Mar. 3, 2016", 6 pgs.
"U.S. Appl. No. 14/496,473, Response filed Apr. 17, 2011 to Non Final Office Action dated Jan. 17, 2017", 14 pgs.
"U.S. Appl. No. 14/496,473, Response filed Jul. 7, 2016 to Non Final Office Action dated Apr. 22, 2016", 12 pgs.
"U.S. Appl. No. 14/496,473, Response filed Jul. 11, 2017 to Final Office Action dated May 11, 2017", 13 pgs.
"U.S. Appl. No. 14/496,473, Response filed Nov. 14, 2016 to Final Office Action dated Sep. 13, 2016", 12 pgs.
"U.S. Appl. No. 14/496,473, Response filed Nov. 30, 2017 to Non Final Office Action dated Aug. 31, 2017", 13 pgs.
"U.S. Appl. No. 14/496,473, Restriction Requirement dated Mar. 3, 2016", 6 pgs.
"U.S. Appl. No. 14/497,815, 312 Amendment filed Mar. 28, 2016", 6 pgs.
"U.S. Appl. No. 14/497,815, Examiner Interview Summary dated Feb. 29, 2016", 3 pgs.
"U.S. Appl. No. 14/497,815, Non Final Office Action dated Dec. 21, 2015", 9 pgs.
"U.S. Appl. No. 14/497,815, Notice of Allowance dated Mar. 21, 2016", 9 pgs.
"U.S. Appl. No. 14/497,815, PTO Response to Rule 312 Communication dated Apr. 6, 2016", 2 pgs.
"U.S. Appl. No. 14/497,815, Response filed Feb. 25, 2016 to Non Final Office Action dated Dec. 21, 2015", 11 pgs.
"U.S. Appl. No. 14/497,815, Response filed Dec. 2, 2015 to Restriction Requirement dated Nov. 23, 2015", 4 pgs.
"U.S. Appl. No. 14/497,815, Restriction Requirement dated Nov. 23, 2015", 7 pgs.
"U.S. Appl. No. 15/095,651, 312 Amendment filed Jun. 8, 2018", 7 pgs.
"U.S. Appl. No. 15/095,651, Non Final Office Action dated Jan. 16, 2018", 9 pgs.
"U.S. Appl. No. 15/095,651, Notice of Allowance dated Mar. 30, 2018", 8 pgs.
"U.S. Appl. No. 15/095,651, Preliminary Amendment filed Apr. 11, 2016", 7 pgs.
"U.S. Appl. No. 15/095,651, PTO Response to 312 Communication dated Jun. 20, 2018", 2 pgs.
"U.S. Appl. No. 15/095,651, Response filed Feb. 21, 2018 to Non Final Office Action dated Jan. 16, 2018", 9 pgs.
"U.S. Appl. No. 15/095,651, Response filed Dec. 5, 2017 to Restriction Requirement dated Nov. 14, 2017", 7 pgs.
"U.S. Appl. No. 15/095,651, Restriction Requirement dated Nov. 14, 2017", 6 pgs.
"U.S. Appl. No. 15/917,212, 312 Amendment filed Sep. 24, 2019", 5 pgs.
"U.S. Appl. No. 15/917,212, Corrected Notice of Allowability dated Sep. 4, 2019", 4 pgs.
"U.S. Appl. No. 15/917,212, Examiner Interview Summary dated May 21, 2019", 3 pgs.
"U.S. Appl. No. 15/917,212, Non Final Office Action dated Mar. 26, 2019", 10 pgs.
"U.S. Appl. No. 15/917,212, Notice of Allowance dated Jul. 15, 2019", 7 pgs.
"U.S. Appl. No. 15/917,212, Notice of Non-Compliant Amendment dated Feb. 15, 2019", 3 pgs.
"U.S. Appl. No. 15/917,212, Preliminary Amendment filed Mar. 9, 2018", 6 pgs.
"U.S. Appl. No. 15/917,212, PTO Response to Rule 312 Communication dated Oct. 17, 2019", 2 pgs.
"U.S. Appl. No. 15/917,212, Response filed Jan. 22, 2019 to Restriction Requirement dated Nov. 27, 2018", 7 pgs.
"U.S. Appl. No. 15/917,212, Response fifed Feb. 26, 2019 to Notice of Non-Compliant Amendment dated Feb. 15, 2019", 8 pgs.
"U.S. Appl. No. 15/917,212, Response filed May 22, 2019 to Non Final Office Action dated Mar. 26, 2019", 13 pgs.
"U.S. Appl. No. 15/917,212, Restriction Requirement dated Nov. 27, 2018", 6 pgs.
"U.S. Appl. No. 16/002,498, Non Final Office Action dated Nov. 5, 2019", 12 pgs.
"U.S. Appl. No. 16/002,498, Notice of Allowance dated Feb. 24, 2020", 7 pgs.
"U.S. Appl. No. 16/002,498, Preliminary Amendment filed Jun. 7, 2018", 5 pgs.
"U.S. Appl. No. 16/002,498, Response filed Feb. 5, 2020 to Non Final Office Action dated Nov. 5, 2019", 11 pgs.
"U.S. Appl. No. 16/106,390, Corrected Notice of Allowability dated Feb. 24, 2020", 4 pgs.
"U.S. Appl. No. 16/106,390, Corrected Notice of Allowability dated Mar. 12, 2020", 5 pgs.

(56) References Cited

OTHER PUBLICATIONS

"U.S. Appl. No. 16/106,390, Non Final Office Action dated May 21, 2019", 15 pgs.
"U.S. Appl. No. 16/106,390, Notice of Allowance dated Dec. 17, 2019", 8 pgs.
"U.S. Appl. No. 16/106,390, Preliminary Amendment filed Aug. 21, 2018", 6 pgs.
"U.S. Appl. No. 16/106,390, Response filed Aug. 21, 2019 to Non Final Office Action dated May 21, 2019", 12 pgs.
"Chinese Application Serial No. 201480047065.X, Office Action dated Sep. 11, 2018", w/ English Translation, 13 pgs.
"Chinese Application Serial No. 201480047065.X, Response filed Feb. 21, 2019 to Office Action dated Sep. 11, 2018", w/o English Translation, 7 pgs.
"Chinese Application Serial No. 201480047065.X, Response filed May 25, 2018 to Office Action dated Mar. 13, 2018", w/o English Translation, 10 pgs.
"Chinese Application Serial No. 201480047065.X, Response filed Nov. 23, 2018 to Office Action dated Sep. 11, 2018", w/o English Translation, 10 pgs.
"Chinese Application Serial No. 201480047342.7, Office Action dated Mar. 27, 2017", w/ English Translation, 24 pgs.
"Chinese Application Serial No. 201480047342.7, Office Action dated May 31, 2018", w/ English Translation, 12 pgs.
"Chinese Application Serial No. 201480047342.7, Office Action dated Dec. 14, 2017", w/ English Translation, 10 pgs.
"Chinese Application Serial No. 201480047342.7, Response filed Jan. 22, 2018 to Office Action dated Dec. 14, 2017", w/o English Translation, 10 pgs.
"Chinese Application Serial No. 201480047342.7, Response filed Aug. 3, 2017 to Office Action dated Mar. 27, 2017", w/o English Translation, 12 pgs.
"Chinese Application Serial No. 201480047342.7, Response filed Aug. 14, 2018 to Office Action dated May 31, 2018", w/o English Translation, 9 pgs.
"Chinese Application Serial No. 201480047342.7, Response filed Sep. 14, 2018 to Office Action dated May 31, 2018", w/o English Translation, 7 pgs.
"European Application Serial No. 14777479.8, Communication Pursuant to Article 94(3) EPC dated May 14, 2019", 6 pgs.
"European Application Serial No. 14777479.8, Communication Pursuant to Article 94(3) EPC dated Dec. 18, 2019", 4 pgs.
"European Application Serial No. 14777479.8, Response filed Sep. 6, 2019 to Communication Pursuant to Article 94(3) EPC dated May 14, 2019", 47 pgs.
"European Application Serial No. 14777479.8, Response to Communication pursuant to Rules 161(1) and 182 EPC filed Sep. 6, 2016", 9 pgs.
"European Application Serial No. 14777479.8,, Response filed Apr. 16, 2020 to Office Action dated Dec. 18, 2019", 6 pgs.
"European Application Serial No. 14781019.6, Communication Pursuant to Article 94(3) EPC dated Dec. 18, 2019", 6 pgs.
"European Application Serial No. 14781019.6, Response filed Apr. 11, 2020 to Communication Pursuant to Article 94(3) EPC dated Dec. 18, 2019", 70 pgs.
"European Application Serial No. 14781019.6, Response filed Aug. 23, 2019 to Communication Pursuant to Article 94(3) EPC dated Apr. 24, 2019", 2 pgs.
"European Application Serial No. 14781019.6, Response filed Sep. 7, 2016", 11 pgs.
"International Application Serial No. PCT/US2014/056890, International Preliminary Report on Patentability dated Apr. 7, 2016", 8 pgs.
"International Application Serial No. PCT/US2014/056890, International Search Report dated Feb. 4, 2015", 5 pgs.
"International Application Serial No. PCT/US2014/056890, Written Opinion dated Feb. 4, 2015", 6 pgs.
"International Application Serial No. PCT/US2014/056911, International Preliminary Report on Patentability dated Apr. 7, 2016", 7 pgs.

"International Application Serial No. PCT/US2014/056911, International Search Report dated Dec. 12, 2014", 4 pgs.
"International Application Serial No. PCT/US2014/056911, Written Opinion dated Dec. 12, 2014", 5 pgs.
"International Application Serial No. PCT/US2014/057429, International Preliminary Report on Patentability dated Apr. 7, 2016", 10 pgs.
"International Application Serial No. PCT/US2014/057429, International Search Report dated Feb. 19, 2015", 5 pgs.
"International Application Serial No. PCT/US2014/057429, Written Opinion dated Feb. 19, 2015", 8 pgs.
"International Application Serial No. PCT/US2014/057659, International Preliminary Report on Patentability dated Apr. 7, 2016", 8 pgs.
"International Application Serial No. PCT/US2014/057659, International Search Report dated Dec. 23, 2014", 4 pgs.
"International Application Serial No. PCT/US2014/057659, Written Opinion dated Dec. 23, 2014", 6 pgs.
"Japanese Application Serial No. 2016-537951, Amendment filed Feb. 26, 2016", W/ English Translation, 6 pgs.
"Japanese Application Serial No. 2016-537951, Decision in Trial to Reject mailed Oct. 23, 2019", w/ English Translation, 54 pgs.
"Japanese Application Serial No. 2016-537951, Decision of Rejection dated Aug. 28, 2018", W/ English Translation, 4 pgs.
"Japanese Application Serial No. 2016-537951, Notice of Reason for Rejection dated Jan. 31, 2017", W/ English Translation, 8 pgs.
"Japanese Application Serial No. 2016-537951, Notice of Reason for Rejection dated May 8, 2018", W/ English Translation, 8 pgs.
"Japanese Application Serial No. 2016-537951, Notice of Reason for Rejection dated Oct. 3, 2017", W/ English Translation, 9 pgs.
"Japanese Application Serial No. 2016-537951, Response filed Apr. 28, 2017 to Notice of Reason for Rejection dated Jan. 31, 2017", W/ English Translation, 19 pgs.
"Japanese Application Serial No. 2016-537951, Response filed Jul. 31, 2018 to Notice of Reason for Rejection dated May 8, 2018", with English translation of claims, 13 pgs.
"Japanese Application Serial No. 2016-537951, Response filed Dec. 5, 2018 to Decision of Rejection dated Aug. 28, 2018", with English translation of claims, 4 pgs.
"Japanese Application Serial No. 2016-537951, Response filed Dec. 28, 2017 to Notice of Reason for Rejection dated Oct. 3, 2017", W/ English Translation, 12 pgs.
"Japanese Application Serial No. 2016-537952, Decision to Grant dated Jan. 23, 2018", English translation, 2 pgs.
"Japanese Application Serial No. 2016-537952, Notice of Reasons for Rejection dated Jan. 31, 2017", with English translation of claims, 12 pgs.
"Japanese Application Serial No. 2016-537952, Response filed May 8, 2017 to Written Opinion dated Apr. 28, 2019", with English translation of claims, 24 pgs.
"Japanese Application Serial No. 2016-537952, Response filed Dec. 21, 2017 to Notice of Reasons for Refusal dated Sep. 27, 2017", with English translation of claims, 11 pgs.
"Japanese Application Serial No. 2016-537952, Written Opinion dated Apr. 28, 2017", with English translation of claims, 19 pgs.
"Japanese Application Serial No. 2016-537952, Written Statement filed May 2, 2017", with English translation of claims, 7 pgs.
"Japanese Application Serial No. 2018-028128, Notice of Reasons for Refusal dated Dec. 18, 2018", with English translation of claims, 6 pgs.
"Japanese Application Serial No. 2018-028128, Written Amendment filed Feb. 20, 2018", with English translation of claims, 4 pgs.
"Japanese Application Serial No. 2018-028128, Written Amendment filed Mar. 14, 2019", with English translation of claims, 2 pgs.
"Japanese Application Serial No. 2019-0878875, Written Amendment filed Jun. 5, 2019", with English translation of claims, 3 pgs.
Cheng, Ming, et al., "Adjustable Endoscope Sheath", Potentially Related Application, U.S. Appl. No. 14/551,440, filed Nov. 24, 2014, 25 pgs.
Konstorum, Gregory, et al., "Oblong Endoscope Sheath", Potentially Related Application U.S. Appl. No. 14/496,473, filed Sep. 25, 2014, 37 pgs.

(56) References Cited

OTHER PUBLICATIONS

"European Application Serial No. 20210311.5, Extended European Search Report dated Mar. 2, 2021", 9 pgs.
"Japanese Application Serial No. 2019-087875, Response filed Apr. 5, 2021 to Office Action dated Jan. 5, 2021", w/English Claims, 12 pgs.

* cited by examiner

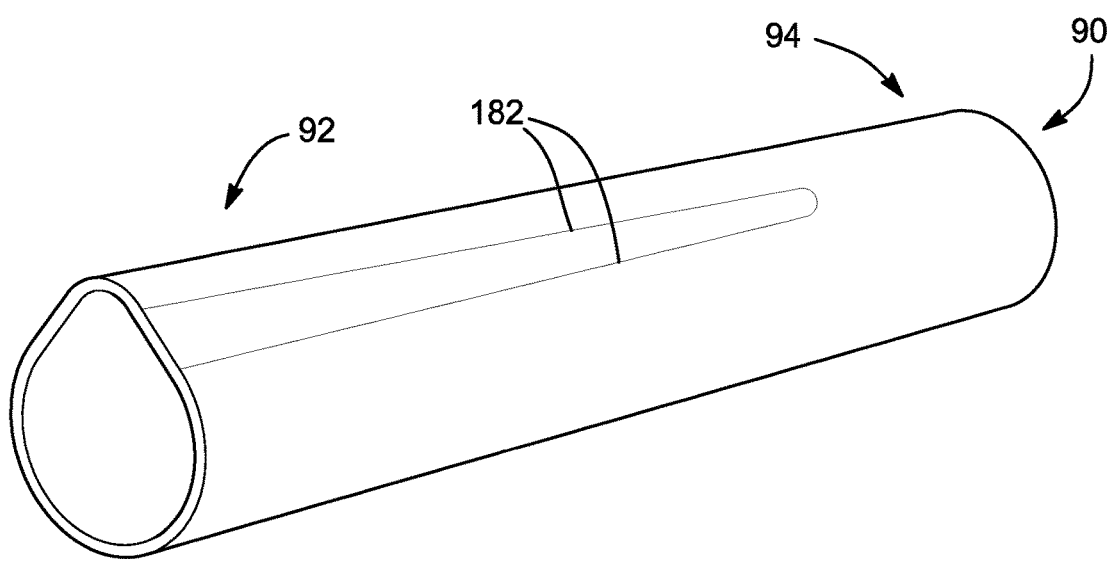
Figure 5A
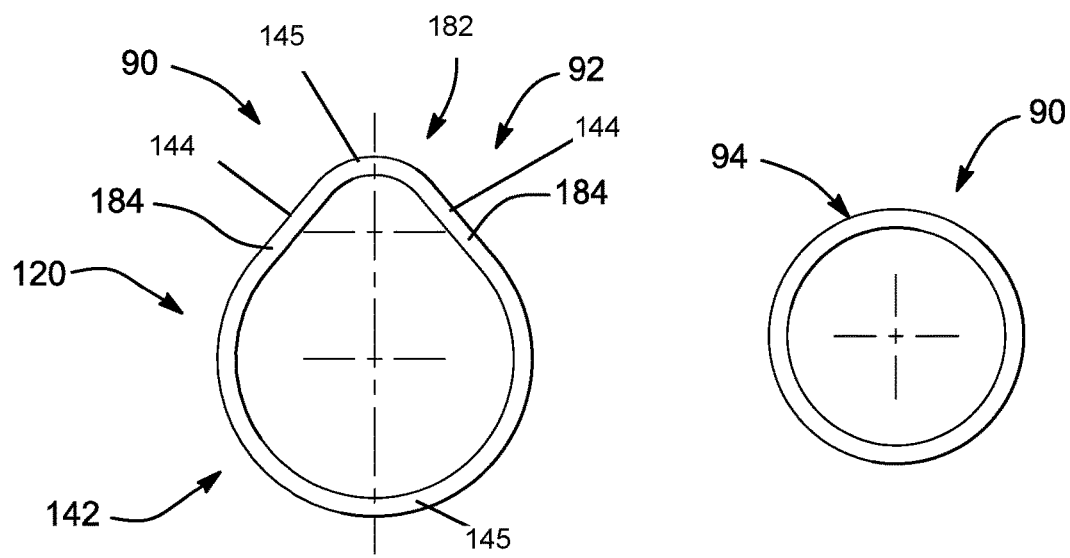
Figure 5B
Figure 5C

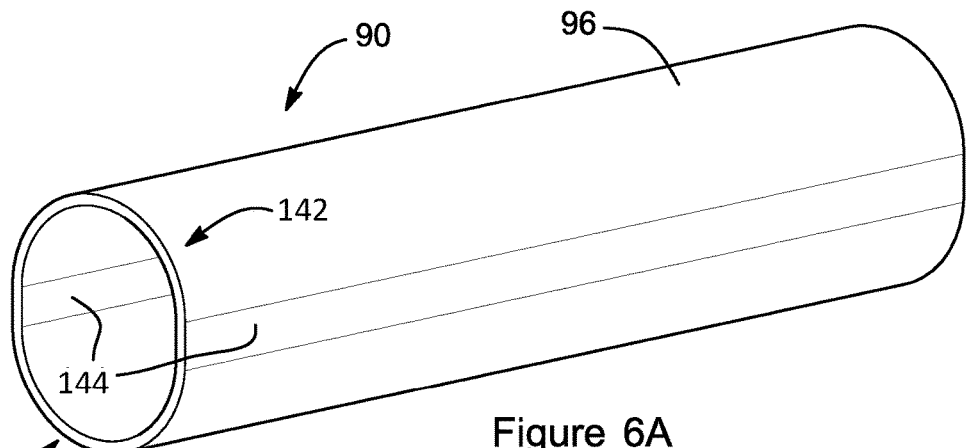
Figure 6A
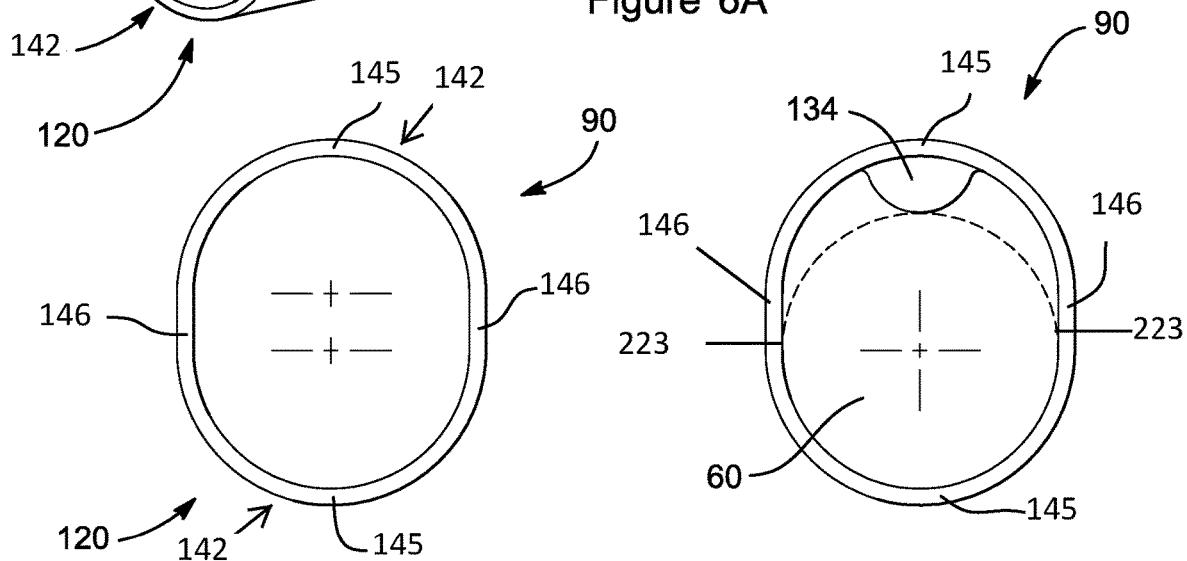
Figure 6B
Figure 6C
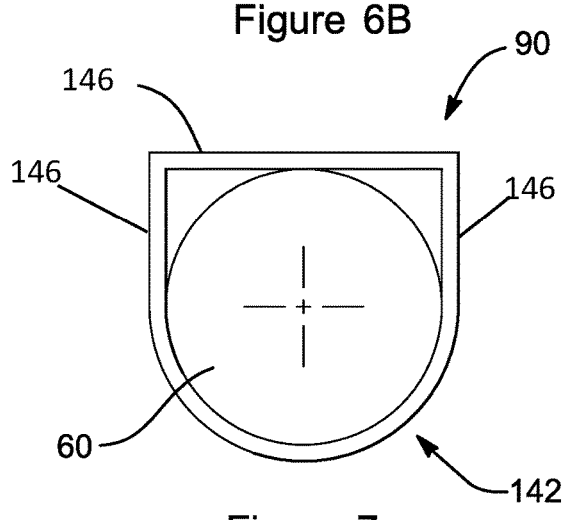
Figure 7
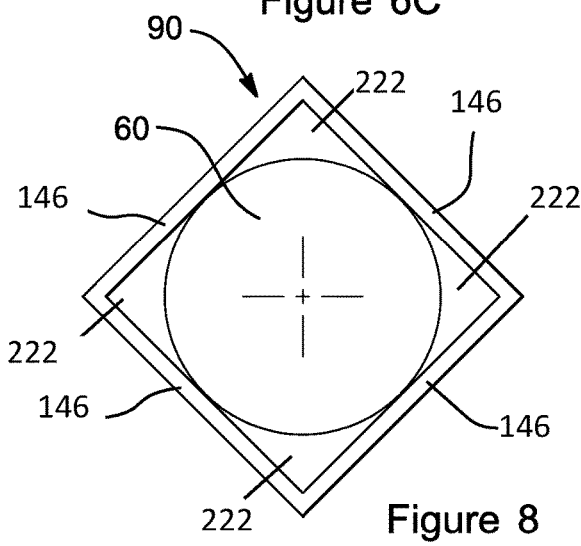
Figure 8

OBLONG ENDOSCOPE SHEATH

FIELD

The present teachings generally relate to an endoscope sheath that receives all or a portion of an endoscope and more specifically to an endoscope sheath that self-aligns the endoscope within the sheath creating a channel, lumen, or both.

BACKGROUND

Endoscopes are typically used for minimally invasive surgery or to provide access to an internal location of a patient so that a doctor is provided with visual access. Endoscopes, during use, may be inserted into a location that may include debris that may cover the end of the endoscope and especially cover an imaging device located at the end of the endoscope. For example, an endoscope being used for surgery may become covered by blood and the blood may impair the vision of a surgeon so that surgery becomes increasingly difficult. Attempts have been made to provide various devices to assist a surgeon in clearing the debris from the imaging device of the endoscope and restore vision. These devices may remove some of the debris from the imaging device of the endoscope, however, these devices may not remove all of the debris and/or may leave spots or droplets on the imaging device, which may result in continued impairment. These devices may have features that attempt to control the flow of fluid, suction, or both at the end of the endoscope in an attempt to clear debris, spots, droplets, or a combination thereof from the endoscope. Further, many of the features at the end of the sheath are configured to align the sheath with the endoscope and these feature perform little if any directing of fluid across the end of the endoscope.

Examples of some endoscope cleaning devices may be found in U.S. Pat. Nos. 5,575,756; 7,708,689; and 8,079,952; and U.S. Patent Application Publication No. 2011/0230716 all of which are incorporated by reference in their entirety herein for all purposes. It would be attractive to have an endoscope sheath that self-aligns the endoscope within the sheath so that a conduit, a lumen, a channel, or a combination thereof is created along all or a portion of the length of the sheath. It would be attractive to have an endoscope sheath that includes a channel that c accommodate fluid, suction, one or more functional elements, or a combination thereof. What is needed is an endoscope sheath that includes one or more non-circular sections that align the endoscope within the sheath and create a channel, conduit, a lumen, or a combination thereof.

SUMMARY

The present teachings meet one or more of the present needs by providing: an endoscope sheath comprising: a proximal end; a distal end having a distal end region; a surface extending between and connecting the proximal end and the distal end; and a plurality of positioning devices located along the surface; wherein the sheath is configured to; (1) receive all or a portion of an endoscope having a cylindrical end and (2) provide a conduit for communicating fluid between the proximal end of the sheath and the distal end of the sheath when the endoscope is inserted inside the sheath; and wherein the distal end region of the sheath includes the plurality of positioning devices that secure the cylindrical end of the endoscope against a portion of an inner wall of the surface extending between the proximal end and the distal end so that a fluid barrier is created between the cylindrical end of the endoscope and the inner wall.

Another possible embodiment of the present teachings comprises: an endoscope cleaner comprising: a sheath having: a proximal end, a distal end, and an inner surface extending between the proximal end and the distal end; wherein the sheath is configured to receive all or a portion of an endoscope and provide a conduit for communicating fluid between the proximal end of the sheath and the distal end of the sheath when the endoscope is inserted inside the sheath, and wherein the distal end of the sheath has a cross-section with a circular portion having a diameter substantially matching a diameter of the endoscope and one or more tangent portions that have one or more segments that are tangent to the circular portion at one or more points.

Yet another possible embodiment of the present teachings provides: an endoscope cleaner comprising: (a) a proximal end, (b) a distal end including: (i) two or more non-unitary positioning, features that are configured to provide an axial end stop for an endoscope, and (c) a surface extending between and connecting the proximal end and the distal end, wherein the two or more non-unitary positioning features are connected to the distal end of the surface by one or more fasteners, adhesives, or both.

The teachings herein provide an endoscope sheath that self-aligns the endoscope within the sheath so that a conduit, a lumen, a channel, or a combination thereof is created along all or a portion of the length of the sheath. The teachings herein provide an endoscope sheath that includes a channel that can accommodate fluid, suction, one or more functional elements, or a combination thereof. The teachings herein provide an endoscope sheath that includes one or more non-circular sections that align the endoscope within the sheath and create a channel conduit, a lumen, car a combination thereof.

BRIEF DESCRIPTION OF THE DRAWINGS

FIG. 5A illustrates a side view of a sheath having a non-circular perimeter along a portion of the length;

FIG. 5B illustrates a distal end view of the sheath of FIG. 5A;

FIG. 5C illustrates a proximal end view of the sheath of FIG. 5A;

FIG. 6A illustrates a perspective view of a sheath having an oblong car obround shape;

FIG. 6B illustrates an end view of the sheath of FIG. 6A;

FIG. 6C illustrates an end view of a sheath including an endoscope;

FIG. 7 illustrates an example of an end view of a sheath including one flat wall;

FIG. 8 illustrates an end view of a sheath have a plurality of flat walls;

DETAILED DESCRIPTION

Figure 1A:
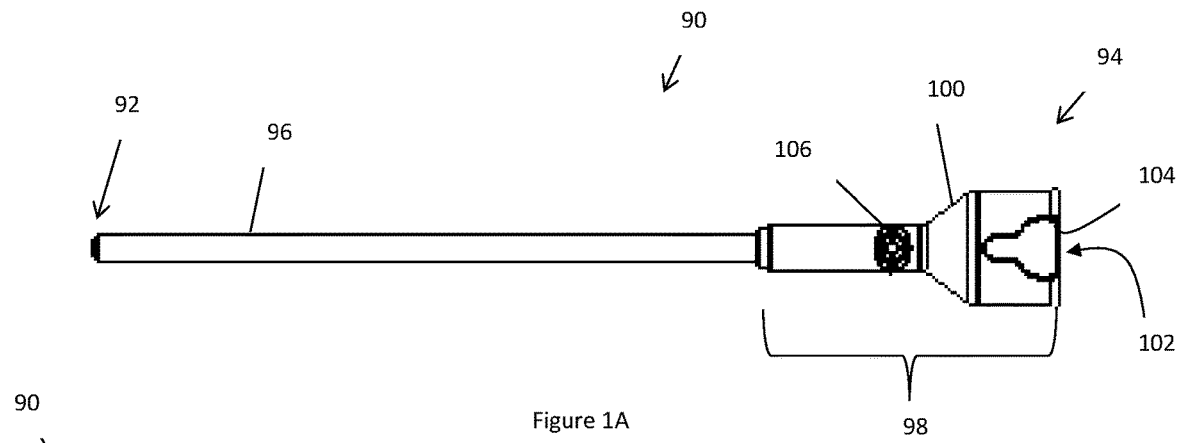
FIG. 1A illustrates a top view of an endoscope sheath.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

The present application claims priority to U.S. Provisional Patent Application Ser. No. 61/882,652, filed on Sep. 26, 2013, the contents of which are incorporated by reference herein in their entirety for ail reasons. The present teachings provide an endoscope sheath for use in a system. The system of the teachings herein includes an irrigation source and a suction source that are both connected to an endoscope sheath that is in communication with an endoscope. The system may include one or more control modules. The system may function to clean an endoscope. Preferably, the system functions to clean a distal tip of an endoscope. More preferably, the system functions to clean an imaging device of an endoscope. The system may include one or more functional components that may extend proximate to a distal end of an endoscope or beyond a distal end of an endoscope. The system may provide one or more conduits relative to the endoscope. The system may protect the endoscope. The system may include one or more sources of irrigation fluid for use with the system, and the one or more sources of irrigation fluid, suction, or both ay be controlled by one or more control modules.

The one or more control modules may function to control the amount of fluid, suction, or both applied to a predetermined area, an area of interest, the endoscope, or a combination thereof. The one or more control modules may be powered by electricity, battery powered, or both. The one or more control modules may include one or more pumps, one or more valves, one or more user interfaces, or a combination thereof. The one or more user interfaces may be one or more control knobs, one or more selectors, one or more indicators, one or more user controls, one or more devices for changing a parameter, or a combination thereof. The one or more control modules may include any of the pumps discussed herein and based upon feedback from the user interface may control the pump to perform the selected parameter. The control module may include a microprocessor, a computer, a control algorithm, or a combination thereof. The control module may control one more valves located within the system, connected to the control module, or both. The one or more control modules may perform a suction function, an irrigation function, or a combination of both upon a selection by the user as is indicated by the user interface. The control module may control the running speed, pumping duration, or both of the pump so that irrigation fluid is moved to the sheath.

The irrigation fluid may function to clean an endoscope, clear debris from a location proximate to the endoscope, be bioabsorbable, or a combination thereof. The irrigation fluid may function to move solid particles, move opaque fluids, or both. The irrigation fluid may be applied with a pressure. The pressure of the irrigation fluid may be varied by changing the height of the irrigation source relative to the sheath so that the head of the irrigation fluid is increased or decreased. The pressure of the irrigation fluid may be sufficiently high so that the irrigation fluid may be redirected by a flow director. The irrigation fluid may be applied with a pressure of about 0.10 MPa or more, about 0.20 MPa or more, about 0.30 MPa or more, or even about 0.50 MPa or more. The irrigation fluid may be applied with a pressure of about 3 MPa or less, about 2 MPa or less, about MPa or less, or even about 0.75 MPa or less. The irrigation fluid may be applied with a sufficient amount of pressure that the surface tension of the irrigation fluid wicks the irrigation fluid across the distal end, the imaging portion, or both of the endoscope (e.g., the pressure may be low enough that the irrigation fluid remains in contact with the endoscope, the sheath, or both). The irrigation fluid may be applied with a gravity feed, thus, the pressure of the irrigation fluid may be determined by the height of an irrigation source. For example, the irrigation source may be an IV bag and the height of the IV bag may determine the amount of pressure and/or force generated at the distal tip of the sheath, endoscope, or both. The irrigation fluid may be applied by a pump that pumps the fluid at a predetermined pressure. The irrigation fluid may be continuously applied, intermittently applied, or both during an application cycle. The pressure of the irrigation fluid may change when the irrigation fluid reaches the end of an endoscope sheath so that the fluid cleans the endoscope, creates turbulence at the end of the endoscope, or both. Preferably, the pressure is sufficiently low so that the flow across the endoscope is laminar. The pressure of the irrigation fluid may be varied based upon the size, length, or both of an irrigation line extending between an irrigation source and the sheath. The irrigation source may be a reservoir that fluid is drawn from by a fluid movement mechanism (e.g., a pump) and moved through the sheath to provide irrigation to a distal end of an endoscope, to clean an endoscope, or both.

The pump may function to circulate irrigation fluid, move irrigation fluid through one or more lines, move fluid through a sheath, or a combination thereof. The pump may function to create a negative pressure (e.g., Suction or vacuum). The pump may move fluid with an impeller. The pump may be a lobe pump, a centrifugal pump, a positive displacement pump, a rotary positive displacement pump, a diaphragm pump, peristaltic pump, rope pump, a gear pump, a screw pump, a progressing cavity pump, a roots-type pump, a plunger pump, or a combination thereof. Preferably, the pump moves a constant amount of fluid upon being activated, a constant amount of fluid may be varied from application to application, or both. More preferably, the pump is a peristaltic pump.

The one or more irrigation lines may function to connect the sheath to an irrigation source. The irrigation lines may function to create a head so that pressure is created and the irrigation fluid is applied with a force. The irrigation line may be flexible, movable, or both. The irrigation line may be made of any material that is compatible with the irrigation fluid, a patient, use in a surgical procedure, or a combination thereof. The irrigation line may connect the sheath to an irrigation source, a suction source, or both (i.e., suction may be applied through the irrigation line).

The suction source may function to remove fluid, debris, opaque fluids, unwanted material, or a combination thereof from a point of interest, from a distal end of the sheath, a distal end of the endoscope, or a combination thereof. The suction source may function to perform a drying function, remove fluid spots, or both. The suction source may be a pump, reversal of a motor, a common suction source, a hospital suction source, or a combination thereof. The suction source may apply a sufficient amount of vacuum to remove a predetermined amount of fluid in a predetermined amount of time. For example, the suction source may apply suction so that 10 ml of fluid may be removed in 1 to 2 seconds. The suction source may apply a continuous suction, intermittent suction, or both.

The suction line may function to connect to the sheath so that suction may be pulled through the sheath. The suction line may function to connect the sheath to a suction source. The suction line may assist is moving fluids, removing fluids, removing debris, removing opaque, fluids, removing particles, or a combination thereof. The suction line may be any line that may assist in creating a vacuum at a distal tip of the endoscope, the sheath, or both. The suction line and the irrigation line may be the same line. The suction line and the irrigation line may be connected to a common line. The suction line and the irrigation line may be connected by one or more fittings, one or more valves or both.

The one or more valves may function to allow only one functions (e.g., irrigation or suction) to work at a time. The one or more valves may function to block the irrigation line, the suction line, or both. The one or more valves may only allow suction or irrigation to be applied at a given time. The one or more valves may be or include a check valve, a back flow preventer, or both. The one or more valves may be located proximate to the sheath, proximate to the irrigation source, proximate to the suction source, or a location therebetween. Each of the lines may include a valve. If more than one valve is present the valves may be electrically connected, hydraulically connected, fluidly connected, or a combination thereof so that if one valve is opened another valve is closed. The two or more valves (e.g., a first valve and a second valve) may be electrically connected, electrically controlled, or both. The two or more valves may be operated in a sequence (e.g., one opened and then one closed), operated simultaneously, operated on a delay, or a combination thereof. For example, only one valve may be open at a time. In another example, one may close and after a time delay another may open. The one or more valves may be part of a common fitting, located proximate to a common fitting, or both.

The one or more common fittings may function to connect two or more lines into a common line. The one or more common fittings may function to connect a suction line and an irrigation line to a common port. The one or more common fittings may connect a single line to multiple devices so that multiple devices may be used simultaneously, in series, in parallel, or a combination thereof. For example, the common fitting may connect a suction line and an irrigation line to a common line that is connected to a sheath and, during operation, an irrigation fluid may be applied and then after a delay and/or immediately when the irrigation fluid ceases to be applied, suction may be applied to the suction line so that irrigation fluid, excess irrigation fluid, debris, particles, opaque fluids, or a combination thereof are removed from the distal end of the endoscope. The one or more common fittings may have two or more openings, three or more openings, four or more openings, or even five or more openings. Each opening may receive at least one line and fluidly connect the one or more lines together. More than one common fitting may be used to connect multiple lines together. For example, a first common fitting with three openings may be connected to second common fitting with three openings so that two tubes are connected to one opening of the first common fitting and one tube is connected to each of the other two openings. Preferably, the common fitting is generally "Y" shaped and two of the openings lead into a third opening that is connected to a common line and/or a delivery line.

The common line may function to deliver irrigation fluid, suction, or both to a sheath. The common line may function to provide a combination of multiple different fluids, devices, suction levels, fluid pressures, or a combination thereof. The common line may provide a single access point between the irrigation source, the suction source, or both and the sheath. The common line may have an increased cross-sectional area (e.g., diameter) relative to the cross-sectional area of the irrigation line, the suction line, or both. The common line may be the same size as one or both of the irrigation line, the suction line, or both. The common line may extend between the common fitting and a port of the sheath. The common line may be a delivery line.

The delivery line may function to deliver fluids to a sheath. The delivery line may function to deliver suction to the sheath. The delivery line and the common line are preferably the same line. The delivery line, common line, or both may be used during, an application cycle.

The application cycle may be any cycle where an endoscope is cleaned. The application cycle may be a cycle where a combination of different items are applied, a combination of different sequences are performed, or both. The application cycle may be a cycle where an irrigation fluid and suction are applied in a sequence to clean an endoscope. The application cycle may be a combination of one or more applications of fluid, one or more applications of suction, or both. The application cycle may be an application of fluid and immediately thereafter an application of suction to remove excess fluid form a point of interest, the distal end of the endoscope, the distal end of the sheath, or a combination thereof. The application cycle may have no delay between an end of the application of an irrigation fluid and the beginning of the application of suction. For example, upon completion of the irrigation fluid being applied the suction may immediately begin. The application cycle may be varied by a user. The application cycle may include only an application of fluid (i.e., a flushing cycle, a washing manner) with no suction. The application cycle may be user activated for a predetermined amount of time. The application cycle may be activated based upon a duration a user activates a switch. For example, a user may pre-set the activation cycle so that one touch of the switch causes the irrigation fluid to run for 5 seconds. The user may pre-set the activation cycle so that no suction is used. The application cycle may concurrent application of fluid and suction. For example, suction may begin being applied before the irrigation fluid is turned off. The application cycle of the irrigation fluid, the suction, or both may be, changed by a user changing a selector, actuating a control longer, changing an input, or a combination thereof. The application cycle may be sufficiently long so that an image sensor of an endoscope is clear and good images may be taken.

The endoscope may function to provide an image to a surgeon, a doctor, a nurse, any other person who desires visual access to a remote location, or a combination thereof. The endoscope may be used for non-invasive surgery. The endoscope may be used, for orthoscopic surgery. The endoscope may be inserted in a cut in tissue. The endoscope may be used for insertion into an orifice including an ear, nose, throat, rectum, or a urethra. The endoscope may have a generally circular cross-section. The endoscope may have a tubular section that is generally cylindrical (i.e., internal portion). The endoscope may have a tubular section extending to the distal end and a handpiece connected to the tube and extending to the proximal end. The endoscope may have a cylindrical distal end. The body of the endoscope and the distal end of the endoscope may be different shapes. The endoscope may include one or more image sensors in a distal end region (i.e. internal portion). The one or more image sensors may be located in an external portion of the endoscope and fiber optics connected to the image sensor may transmit a signal through the internal portion to the external portion. The endoscope may include two or more image sensors. The endoscope may include an image sensor at the most distal point of the endoscope. The endoscope may include an image sensor that is located on an angle. The angle of the image sensor, viewing face, or both may be about 0°, 20°, 30°, 45°, 60°, 70°, or a combination thereof. The image sensor may provide black and white images, color images, thermal images, or a combination thereof. Preferably, the image sensor, imaging device, or both are located substantially at the distal end. The angle of the image sensor, the viewing face, or both may dictate the angle, shape, viewing cone, or a combination thereof of the endoscope.

The viewing cone may be an area of visibility of the endoscope. The viewing cone may be variable, adjustable, or both. The angle of the viewing cone may be movable. The angle of the viewing cone may be predetermined based upon the type of endoscope selected. The angle of the viewing cone may not be affected by the flow director, lumen, sheath, or a combination thereof. The location of the endoscope within the sheath may vary based upon the angle of the viewing cone. For example, the shape of the sheath may offset the endoscope to one side more or less based upon the angle of the viewing cone so that the endoscope sheath does not interfere with the imaging of the endoscope. The viewing cone may extend outward from the distal end of the endoscope in a cone shape.

The distal end of the endoscope may function to be inserted into a patient so that a feature of interest may be viewed through minimally invasive means. The distal end of the endoscope may be the leading portion of the endoscope (i.e., the first portion that enters a patient). The distal end may function to provide washing functions, suction functions, irrigating functions, or a combination thereof that direct the irrigation fluid and suction across the viewing face of the endoscope, the lens, or both. The distal end may include one or more openings. The one or more openings may be at the very end of the distal end (e.g., a 0 degree opening). The one or more opening may be in a sidewall of the sheath, the tube, or both (e.g., 15 degrees, 20 degrees, 30 degrees, 45 degrees, 60 degrees, 70 degrees). The one or more openings may extend into the one or more openings so that a feature of interest may be viewed through the opening. The opening may extend at an angle as the opening extends from the proximal end towards the distal end. The opening may extend at a downward angle so that when an angled endoscope is inserted into the sheath the sheath does not interfere with viewing a feature of interest. The distal end of the endoscope may be on an opposing end of the endoscope as a proximal end. The proximal end may function to be gripped by a user. The proximal end may function to provide controls to a user. The proximal end may provide an interface for connecting, other functional components such as an imaging device (e.g., a camera). The proximal end may function to provide power, sensing, suction, fluid, control, a connection point to outside devices, or a combination thereof to the distal end of the endoscope. The proximal end may be retained out of the patient and the distal end may be inserted in the patent. A shoulder may be located between the distal end and the proximal end.

The shoulder may function to prevent the proximal end from entering a patient. The shoulder may function to form a connection point with a tube of the endoscope. The shoulder may be a terminal portion of a proximal end of the endoscope. The shoulder may prevent a sheath from axially moving towards the proximal end of the endoscope. The shoulder may be a distal end of the proximal end portion of the endoscope. The shoulder may be generally vertical, generally flat, generally orthogonal to the longitudinal axis of the tubular section of the sheath, or a combination thereof. One or more light posts may be located in a distal end region of the proximal portion of the endoscope and the light post may be located on a proximal portion of the endoscope relative to the shoulder (e.g., between the shoulder a visual port but closer to the shoulder end then a visual port end).

The light post may function to provide light into the endoscope. The light post may direct light into the endoscope and out of the tube of the endoscope so that a feature of interest is illuminated. The light post may provide light so that a user can see features of interests that are located in low light conditions. The light post may be rigid. The light post may be immobile and/or fixedly connected to the endoscope so that the light post has a fixed position on the endoscope. The light post may be made of metal, plastic, a biocompatible material, or a combination thereof. The light post may be integral with a main portion of the proximal end. The light post may be made of metal and some other biocompatible material. The one or more light posts may provide light through the endoscope, so that the visual port may be used for observing a feature of interest at a distal end of the endoscope.

The visual port may function to provide a viewing window for a user. The visual port may function to allow a user to observe a feature of interest. The visual port may function to provide an output so that an image is displayed on a monitor. The visual port may provide visual access through the endoscope to a user. The visual port may extend into one or more openings in the sheath, a tube of the sheath, or both. The angle of the openings discussed herein may be complementary to the angle of the visual port of the endoscope. For example, a zero degree endoscope may fit in a zero degree sheath and a 70 degree endoscope may extend into a 70 degree sheath. The visual port may provide a connection point to a camera that displays the image on a larger image device such as a television or a monitor. The visual port may be an optical window at the proximal end that provides visual access to a viewing lens at the distal end.

The viewing lens may function to provide, a window that an image sensor views through. The viewing lens may function to protect an image sensor (e.g., a camera). The viewing lens may be a cover over an image sensor. The viewing lens may be a viewing face of the endoscope and vice versa. The viewing face may be a surface of the endoscope that an image is generated through. The viewing lens may have a cross-sectional length (e.g., diameter) that is less than the cross-sectional length of the endoscope. The viewing lens may have a largest dimension that is larger than the cross-sectional thickness of the endoscope. For example, when the endoscope has an imaging device at a 70° angle the viewing lens may be greater than the cross-sectional length of the endoscope. The viewing tens may protect the imaging device (e.g., camera) from fluid, damage, corrosion, or a combination thereof. The viewing lens may cover one or more imaging devices or even two or more imaging devices. The viewing lens when in use may become covered with debris, fluid, blood, opaque fluids or a combination thereof. The viewing lens may be inhibited from allowing a clear image to be formed. The viewing lens may be partially or fully covered by a sheath, be partially or fully surrounded by a sheath, or both. Preferably, the sheath is located proximate to the viewing lens without interfering with the range of vision, created by the viewing lens.

The sheath may function to provide one or more conduits, lumen, channels, or a combination thereof for a fluid, suction, a functional device (e.g., a cutting tool, cauterizing tool, Or both), or a combination thereof to extend out of a distal end region of the sheath. The one or more conduits, lumen, channels, or a combination thereof may be a gap between the sheath and the endoscope when viewed in the cross-section. The sheath may function to form all or a portion of a conduit, channel, lumen, or a combination thereof for fluid, suction, a functional device, or a combination thereof to extend out of a distal end region of the sheath. The sheath may function to provide cleaning, washing, or both of an endoscope. The sheath may provide a conduit, channel, a lumen, or a combination thereof that extends from a proximal end to a distal end. The sheath may include one or more lumen, create one or more lumen, or both. The sheath may include one or more parts that when connected together create a conduit that provides irrigation fluid, suction, a functional device, or a combination thereof to a distal end of the endoscope. The sheath may substantially mirror the shape of the endoscope. Thus, for example, if the endoscope has a circular cross-section then the sheath has a circular cross section. Preferably, the sheath has a non-circular cross-section. More preferably, the sheath has an oblong, cross-section, includes one or more tangent segments, oblique segments, or both. The oblong cross-section may have a length that is greater than the width, have two circular portions that include separate centers, or both. The length may be a factor larger than the width. The length may be a factor greater than the width of about 1.2 w or more, about 1.5 w or more, about 1.75 w or more, or even about 2 w or more (where "w" is width). The oblong cross-section may be generally oval, include one or more linear segments, or both. The oblong cross-section may include one non-circular portion that includes at least two circular segments and one or more linear segments. The oblong cross-section may have a perimeter that spans 360 degrees. The oblong cross-section may have a portion with an inner diameter that is substantially the same as the outer diameter of the endoscope and a portion with an inner diameter that is smaller than the outer diameter of the endoscope. The sheath may function as an endoscope cleaner. The sheath may have a distal end and a proximal end with a longitudinal axis that extends therebetween.

The distal end of the sheath may function to direct irrigation fluid, suction, or both across the viewing lens, the distal end, or both of the endoscope. The distal end may function to open, be open, or both so that irrigation fluid may exit the sheath. The distal end may function to not interfere with the imaging capabilities of the endoscope. The distal end may open out, so that pressure of the irrigation fluid drops as the irrigation fluid reaches the distal end. The distal end may be free of any integrally formed pieces that direct irrigation fluid, suction, or both across a distal end of the endoscope. The distal end may be free of any extensions that extend from the distal end. The distal end may be free of any pieces that extend from a portion of a distal most end of the sheath. The distal end may be substantially equal around a circumference of the sheath. The distal end may include one or more positioning features (e.g., dimples or pins). The endoscope may be eccentrically located within the distal end. The distal end region may include one or more annular gaps (e.g., a ring shaped gap).

The sheath may include one or more lips. The one or more lips may be a flow director. The one or more lips may function to assist in directing irrigation fluid across the lens, imaging device, or both of the endoscope. The one or more lips may function to substantially mirror the shape of the endoscope. The one or More lips may overhang the endoscope. The one or more Ups may provide a protective cover for the endoscope. The one or more lips may only be used when a flexible flap is used. The one or more lips may function as a distal end stop. The sheath may be free of lips. The one or more lips may be located on a distal end opposite a proximal end of the sheath.

The proximal end of the sheath may function to create a connection with the endoscope. The proximal end may align the sheath relative to the endoscope. The proximal end of the sheath may axially align the sheath, relative to the endoscope, radially align the sheath relative to the endoscope, axially align the distal ends of the sheath and the endoscope, the sheath axially relative to a light post of the endoscope, the sheath rotationally relative to a light post of the endoscope, or a combination thereof. The proximal end may receive all or a portion of the endoscope. The proximal end may contact a shoulder of the endoscope. A longitudinal axis may extend between the proximal end and the distal end of the sheath. The longitudinal axis may extend through a through hole, channel, lumen, or a combination thereof that extends the length of the sheath. The endoscope may extend within the sheath along the longitudinal axis. The longitudinal axis may extend from a connection point between the endoscope and the sheath and through a tube of the sheath.

The tube may function to receive the imaging device of the endoscope. The tube may be located at the distal end of the endoscope. The tube may be generally the same size and shape as the endoscope. For example, if the endoscope has a generally circular cross-section then the tube may have a generally circular cross-section. The tube may have a shape that is different than the endoscope. The tube may be any shape so that the tube is configured to receive the endoscope. The tube may be connected to; a hub, integrally formed with a hub, in fluid communication with a port, connected to a port, include a through hole that is in communication with a port, or a combination thereof. The tube may be connected to a handpiece at the proximal end. The tube has a longitudinal axis and the shape of the tube may be consistent along its length. The shape of the tube may vary along the length of the tube. The tube may be integrally formed with a handpiece. The tube may have a uniform wall thickness, a variable wall thickness, or both. The wall thickness may vary along the length of the tube. The wall thickness may vary along the circumference of the tube. For example, the tube may have a wall that is twice as thick on a bottom half of the tube as a top half of a tube when viewing the tube in a cross-section. The tube may include one or more positioning devices along its length and/or circumference. The one or more positioning devices may be one or more dimples, one or more pins, one or more crimps, one or more end stops, or a combination thereof.

The one or more positioning devices may function to position an endoscope within a sheath. The one or more positioning devices may function to axially align, radially align, longitudinally align, laterally align, or a combination thereof the endoscope within a sheath. The one or more positioning devices may extend along a portion of the length or the full length of the sheath, the tube of the sheath, or both (e.g., a surface of the tube). The one or more positioning devices may be located continuously between the distal end and proximal end of the sheath, periodically be located between the distal end and the proximal end of the sheath, or a combination of both. The one or more positioning devices may be spaced apart. The one or more positioning devices may be circumferentially spaced apart, longitudinally spaced part, laterally spaced apart, coplanar, non-coplanar, or a combination thereof. The one or more positioning devices may be in a line such that each of the positioning devices are coplanar and perpendicular to the longitudinal axis. The one or more positioning devices may be staggered and coplanar (e.g., circumferentially spaced apart and longitudinally spaced apart). The one or more positioning devices may be staggered and non-coplanar. The positioning devices may only be located in the distal end region, proximate to the distal end region, on the distal end side of the sheath, or a combination thereof. The positioning may be positioned in groups and/or sets.

One group of positioning devices may maintain the endoscope a distance from the end of the sheath. The distance may be a sufficient distance so that the irrigation fluids are moved across the lens, imaging device, or both by surface tension. The distance between the distal end of the sheath and the distal end of the endoscope may be a distance so that surface tension moves an irrigation fluid across the lens, the imaging device, or both. For example, surface tension may cause the irrigation fluid to wrap around the imaging device, lens, or both of the endoscope so that the endoscope is cleaned. The distance between the distal end of the endoscope and the distal end of the sheath may be about 1 mm or more, about 2 mm or more, or about 3 mm or more. The distance between the distal end of the endoscope and the distal end of the sheath may be about 15 mm or less, about 12 mm or less, or about 10 mm or less. The surface tension may maintain fluid in contact with the lens, the imaging device, or both so that the lens, the imaging device, or both are washed, cleaned, or both. The one or more positioning devices may both axially align the endoscope and position the endoscope within the sheath, the tube, or both.

The one or more positioning devices may align the endoscope within the tube, the sheath, or both. The one or more and preferably a plurality of positioning devices may create an annular gap around an endoscope. The annular gap may be uniform around the endoscope. The annular gap may vary in distance between the outer wall of the endoscope and the inner wall of the sheath. The one or more and preferably a plurality of positioning devices may move the endoscope into contact with a wall of a sheath, a tube, or both so that a gap is only created around a portion of the endoscope, a fluid is prevented from extending between a contact location between the endoscope and sheath, or both. An offset gap may be created so that a center of the sheath and a center of the endoscope are offset, eccentric, shifted relative to each other, or a combination thereof. For example, the endoscope may be shifted all the way to one wall so that a gap is only located on one side of the endoscope. The one or more positioning devices may function to be an axial stop. The one or more positioning devices may move the endoscope into contact with a surface (e.g., the tube, the sheath or both) so that a fluid barrier is created.

The fluid barrier may function to prevent fluid from flowing between the endoscope and the sheath, the tube, a surface of the sheath and/or tube, or a combination thereof. The fluid barrier may prevent fluid from passing around a portion of the endoscope (e.g., an arc length of 15 degrees or more, 30 degrees or more, 45 degrees, or more, 60 degrees or more, 105 degrees or more, 135 degrees or more, or even about 180 degrees or less). The fluid barrier may be a seal that prevents fluid from passing axially around a portion of the endoscope. The fluid barrier may prevent passage of irrigation fluid, suction, or both between a distal end and a proximal end of the surface, the tube, the sheath, or a combination thereof. The fluid barrier may be located adjacent to a channel, a conduit, a lumen, or a combination thereof. The fluid barrier may only be created when the endoscope is eccentrically located within the tube of the sheath. The positioning devices may move the endoscope so that an arc length of the endoscope is in contact with the tube of the sheath (e.g., barrier portion). The arc length of the endoscope in contact with the tube of the sheath may be about 30 degrees or more, about 45 degrees or more, about 60 degrees or more, about 75 degrees or more, about 90 degrees or more, or even about 105 degrees or more. The arc length of the endoscope in contact with the tube of the sheath may be about 180 degrees or less, about 165 degrees or less, or about 135 degrees or less. The arc length may form a cradle that wraps around and retains an endoscope within a portion of the tube and/or sheath. The cradle may be a circular portion and/or circular segment. The cradle may be connected to an opposing cradle by two straight segments (i.e., tangent segments, oblique segments, or both). The cradle may be part of an obround tube. The cradle may have an arc length as is discussed herein. The cradle may extend from about 30 degrees to about 180 degrees and, preferably from about 60 degrees to about 180 degrees. The one or more positioning devices may be a unitary part, a non-unitary part, or both that positions the endoscope within the tube of the sheath.

The positioning devices may be an integral part, a unitary part, a non-unitary part, or a combination thereof of the sheath. The positioning devices may be added to the sheath, the tube, or both (i.e., non-unitary). The positioning devices may be a non-welded piece, non-soldered piece, or both that is added to the sheath, the tube, or both. The positioning devices may be an added piece of material that is connected to the sheath, the tube, or both. The positioning devices may be added without heating the positioning devices, the tube, the sheath, or a combination thereof (i.e., liquefying material or adding molten material). The positioning devices may be connected to the sheath, the tube of the sheath, or both by one or more fasteners. The positioning devices may be connected to the tube, the sheath, or both by an adhesive, a threaded connection, a rivet like connection, a friction fit, a mating member that extends through the tube and/or sheath, or a combination thereof. The positioning devices may form a connection so that the positioning features extend out from an inside wall of the tube and/or sheath and form a substantially flush connection with an outside wall of the tube.

The one or more positioning devices may be a formed part of the sheath, the tube, or both such that no additional material is added (i.e., unitary). The one or more positioning devices may be a portion that is dented, formed, crushed, pressed, molded, or a combination thereof. The one or more positioning devices may be created by cutting a portion of the sheath, the tube, or both and repositioning the piece of cut material (e.g., a crimp). The sheath may be formed so that the sheath includes one or more positioning devices. The sheath may include a plurality of positioning devices. The positioning devices may be located on an inner wall, an outer wall, be part of the wall, extend through the wall, or a combination thereof of the sheath and/or tube.

The sheath may include one more sets and/or groups of positioning devices. Preferably, the sheath includes two or more sets and/or groups of positioning devices. More preferably, each of the two or more sets and/or groups of positioning devices include two or more positioning devices. For example, one set of two or more positioning devices may be located in the distal end region (i.e., last 10 percent of the sheath) and another set of two or more positioning devices may be located between the distal end region and the proximal end. When more than one positioning device is present the positioning devices may be located at angle relative to each other. The two or more positioning devices may be equally spaced apart. For example, if there are two positioning devices the devices may be 180 degrees apart and there are three positioning devices the positioning devices may be 120 degrees apart. The two or more positioning devices may be spaced apart about 15 degrees or more, about 30 degrees, or more, about 45 degrees or more, about 60 degrees or more, about 90 degrees or more, about 120 degrees or more, or even about 150 degrees or more apart. The two or more positioning devices may be located about 180 degrees or less or about 160 degrees or less apart.

Each sheath may include one or more groups/sets, two or more groups/sets, three or more groups/sets, or even four or more groups/sets of positioning devices. Each group of sets may include one or more, two or more, three or more, or even four or more positioning devices. Each of the groups/sets of positioning devices may be aligned along an axis, offset along an axis, rotationally offset, rotationally aligned, coplanar, non-coplanar, or a combination thereof relative to another group/set of positioning devices. Preferably, each group/set of positioning devices may be substantially the same distance from the distal end, the proximal end, or both. Each of the groups/sets of positioning devices may be aligned along an axis, offset along an axis, rotationally offset, rotationally aligned or a combination thereof within a group. The positioning devices may be a circular portion, a circular segment, a dimple, a pin, a crimp, an end stop, a tangent portion, a tangent segment (or line), an, oblique portion, an oblique segment (or line), or a combination thereof and the teachings as to the positioning devices are incorporated by reference herein for each of the various types of positioning devices.

The one or more dimples may function to position an endoscope within a sheath, a tube of the sheath, or both. The one or more dimples may function to axially position the endoscope within the sheath (e.g., form an axial stop). The one or more dimples may function as a distal end stop, a locator, an axial locator, a cross-sectional locator (e.g., shift the sheath within the cross-section of the sheath), or a combination thereof. For example, the one or more dimples may be used to create an annular gap, an offset gap, or both. The one or more dimples may contact a point of the endoscope along the length of the endoscope. The one or more dimples may function to position the endoscope within the sheath so that a conduit, channel, lumen, space, or a combination thereof is created along all or a portion of the longitudinal axis of the endoscope, sheath, or both. The one or more dimples may create a space, a conduit, a lumen, a channel, or a combination thereof between a wall of the sheath and the endoscope. The one or more dimples may be a portion of the wall of the sheath that extends inward (e.g., towards a center of the sheath). The one or more dimples may be generally round, square, oval, triangular, rounded, have a flat surface, have a rounded surface, be hemispherical, or a combination thereof. The one or more dimples may be an indentation and/or deformation in the side of the sheath, the tube, or both without adding material, without removing material, without relocating material, or a combination thereof. The one or more dimples may be located on opposing sides of the tube. The one or more dimples may be radially spaced apart, axially spaced apart, longitudinally spaced apart, or a combination thereof. The one or more dimples may be located along the length. For example, the tube may include dimples that are spaced apart from the proximal end to the distal end so that the endoscope and sheath are fully supported relative to each other along their respective lengths. If more than one dimple is present the dimples may be located adjacent, in the same plane, in a line, be axially spaced apart, radially spaced apart, coplanar, non-coplanar, or a combination thereof. When more than one dimple is present the dimples may be in a straight line relative to the longitudinal axis, perpendicular to the longitudinal axis, at an angle relative to the longitudinal axis, or a combination thereof. When more than one dimple is present the dimples may be separated by an angle of about 180 degrees or less, about 150 degrees or less, about 120 degrees or less, about 90 degrees or less, or even about 60 degrees or less. The two or more dimples may be separated by an angle of about 15 degrees or more, about 30 degrees or more, or even about 45 degrees or more. The sheath may include about 2 or more dimples, 3 or more dimples, 4 or more dimples, 5 or more dimples, or even about 6 or more dimples. Two or more dimples may be located generally within the plane and radially spaced apart so that the dimples offset the endoscope within the sheath (e.g., the center of the endoscope and the center of the sheet are not in line). The one or more dimples may be located on the same side of the sheath as the port, opposite side of the sheath as the port, at an angle relative to the port, or a combination thereof. The one or more dimples may be used in conjunction with one or more tangent segments, one or more oblique segments, one or more pins, one or more crimps, one or more end stops, or a combination thereof.

The one or more pins may function to bolster the distal end of the sheath the tube, or both. The one or more pins may function to provide an axial end stop. The one or more pins may function to provide axial stability to the endoscope so that that endoscope cannot be forced in an axial direction. The one or more pins may be a non-unitary part, a non-integral part, or both that is added to the sheath, the tube, or both. The one or more pins may be connected to the tube, the sheath, or both using one or more of the fasteners discussed herein. The one or more pins may be connected to the sheath, the tube, or both without a welded connection. The one or more pins may connect to the tube, the sheath, or both so that so that the pins are flush with an outer surface of the tube, the sheath, or both. When more than one pin is present the pins may be the same size and/or different sizes. The cross-sectional length of the pins may be varied. For example, the base may be larger than the tip. The one or more pins may provide a higher axial stiffness when compared to a dimple. The one or more pins may be smaller than a dimple. The one or more pins may be longer than a dimple (i.e., extend further towards a center of the tube and/or sheath than a dimple). The one or more pins may be located at an end of the distal end. For example, the pins may be located closer to the end when compared to a dimple. The one or more pins may have a portion that provides axial alignment and a portion that includes radial alignment.

The one or more pins, one or more crimps, one or more end stops, or a combination thereof may function to prevent axial movement of an endoscope within the sheath, a tube of the sheath, or both. Preferably, the one or more pins one or more crimps, one or more end stops, or a combination thereof may prevent axial movement towards the distal end. The one or more pins, one or more crimps, one or more end stops, or a combination thereof may function to create a gap between the sheath and the endoscope. The one or more pins, one or more crimps, one or more end stops, or a combination thereof may offset the endoscope within the sheath so that the gap is located around a portion of the endoscope (i.e., the gap is not an annular gap). The one or more pins, one or more end stops, or both may be added to the sheath and the pins may extend towards a center of the endoscope.

The one or more crimps may be material that is cut and folded. The one or more crimps may function to be an axial end stop. The one or more crimps may function to position an endoscope within the sheath, the tube, or both. The one or more crimps may be bent from a terminal end inwards and extend in the direction of the longitudinal axis. The one or more crimps may extend from the terminal end and may be angled towards a center of the sheath, the tube, or both. For example, an end of the crimp may be folded sideways inwards so that the crimp points towards an opposing wall and/or opposing crimp. The one or more crimps may be added material that is shaped to create an axial stop, to locate the endoscope within the sheath, or both. The one or more end stops may be material that is welded, adhered, soldered, brazed, or a combination thereof to the end of the sheath, or a combination thereof. When more than one pin, one or more crimps, one or more end stops, or a combination thereof is present the length may be varied, the same, or both. The pins, one or more crimps, one or more end stops, or a combination thereof may maintain the endoscope a distance from the distal edge of the endoscope. The one or more pins may be used in conjunction with one or more dimples, one or more crimps, or both.

The one or more tangent segment may function to decrease the size, diameter, arc, length, or a combination thereof of the sheath at one or more locations. The one or more tangent segments may function to create a cross-sectional area of the sheath that is smaller than the endoscope, a cross-sectional area greater than the endoscope, or both so that the endoscope is positioned at an offset within the sheath. The one or more tangent segments may function to create a space, a lumen, a channel, an opening, a gap, or a combination thereof so that a functional device, irrigation fluid, suction, debris, or a combination thereof may pass through the sheath. The one or more tangent portions, tangent segments, or both may create a sheath with a cross-sectional shape that is non-circular, oblong, egg shaped, oval, ellipse, obround, or a combination thereof. The one or more tangent segments may include a point of contact with the endoscope when viewed in the cross-section. The one or more tangent segments may be generally planar. The one or more tangent portions may be a line and/or segment when viewed in the cross-section. The one or more tangent segments may extend at an angle relative to the perimeter (i.e., outside) of the endoscope when viewed in the cross-section. When more than one tangent lines are used the tangent lines may diverge on one end and converge on the other end. When two or more tangent lines are used any angle is formed between the tangent lines so that a channel, lumen, space, opening, conduit, gap, or a combination thereof are formed. The angle of the tangent portion may be about 15 degrees or more, about 30 degrees or more, about 45 degrees or more, or about 60 degrees or more relative to a plane that bisects the sheath. The angle of the tangent portion may be about 160 degrees or less, about 125 degrees or less, or even about 105 degrees or less relative to a plane that bisects the sheath. For example, the tangent segments extend at an angle relative to a plane that bisects the sheath along its longitude when viewed in the cross-section. The one or more tangent segments may be a tangent line or tangent plane that extends along all or a portion of the sheath.

The tangent portion may function to run the length of the sheath and form a tangent segment when viewed in the cross-section. The tangent portion may be a plane that extend along all or a portion of the length of the sheath. The tangent portion may include a top portion and a bottom portion where an angle and/or shape of the tube changes. The tangent portion may include a change in shape between the tangent portion and the circular portion, between the circular segment and the tangent segment, or both. For example, a crease may be formed in the sheath and the crease may be one or more edges of the tangent portion. The tangent portion may have a pair of opposing edges that are generally parallel and a part of the sheath between the edges forms a line of contact with the endoscope so that the endoscope is shifted, positioned, moved, aligned, or a combination thereof within the sheath.

The tangent portion may include one or more tangent segments. The tangent portions are a part of the tube of the sheath when the sheath is viewed and discussed herein in three dimensions and the tangent segments and/or tangent lines are a part of the tube of the sheath when viewed and discussed herein as two dimensional (i.e., viewed in the cross-section). The tangent portion may include one or more tangent segments that align an endoscope with a sheath. The tangent portion may function to align an endoscope within a sheath. The tangent portion may function to locate an endoscope along a top, bottom, left, or right side of the sheath. The tangent portion may locate the endoscope so that a center of the endoscope and the center of the sheath are offset. The tangent portion may be shaped so that the sheath has an oblong shape, is non-circular one or more flat walls, one or more linear walls, one or more walls with a single point (or line) of contact with an endoscope, or a combination thereof. The tangent portion may assist in forming a lumen, a channel, a conduit, or a combination thereof within the sheath, between the sheath and the endoscope, or both. The tangent portion may have two or more tangent segments that extend at an angle relative to each other. The tangent segments may include one or more circular segments, one or more tangent segments, or both.

The one or more tangent segments may function to extend between a first end and a second end so that a conduit, lumen, channel, a gap, or a combination thereof is created within the sheath. The one or more tangent segments as discussed herein, unless otherwise stated, are discussed in a cross-section, but are part of a larger portion that extends partially or fully along a length of the sheath. The one or more tangent segments may function to align the endoscope within the sheath. The one or more tangent segments may contact the endoscope at a point so that the endoscope is shifted within the sheath. Preferably, the sheath includes two tangent segments that angle towards each other on one end and diverge away from each other on a second end. The one or more tangent segments may be generally planar, linear, or both. The one or more tangent segments may be concave, convex, include a concave portion, a convex portion, or a combination thereof. The one or more tangent segments may, directly connect. For example, the sheath may not include a circular segment and the tangent segments may connection together forming a tube with a conduit, lumen, channel, gap, or a combination thereof. The tangent segments may be free of a connection with a circular segment. The one or more tangent segments may connect two opposing circular segments. The one or more tangent segments may have a tangent point with each of the one or more circular segments. The one or more tangent segments may have a tangent point with both the endoscope and the circular segments. The one or more tangent segments, may extend between a circular portion and a circular segment.

The one or more circular segments may be connected to a tangent segment on one or both sides, a oblique segment on one or both sides, or both. The circular segments as discussed herein, unless otherwise stated, are discussed in the cross-section, but are a part of a larger portion that extends partially or fully along a length of the sheath. The circular segment may have a radius that is substantially the same as the radius of the endoscope (i.e., slightly larger so that the endoscope fits within the sheath). The circular segment may have a radius that is greater than the radius of the endoscope. Preferably, at least one circular segment has a radius that is less than the radius of the endoscope so that the tangent segments diverge and contact the endoscope and a channel, a lumen, a conduit, gap, or a combination thereof is formed between the circular segment and the endoscope. More preferably, at least one of the circular segments has a radius that is greater than the radius of the endoscope and at least one of the circular segments has a radius that is less than the radius of the endoscope. The one or more circular segments may have a center that aligns with a center of the endoscope. Preferably, the center of the endoscope and the center of the circular segments are offset so that the endoscope is shifted to one side and/or end of the tube. The one or more circular segments may be a continuous arc, have a plurality of linear portions that are connected together in an arcuate pattern, or both. The one or more circular segments may function to connect to two segments that generally face in the same direction. The one or more circular segments may have two ends that generally point in the same direction. The one or more circular segments may have a first end and a second end that are, about 180 degrees or more from each other. The first end and the second end may be located about 90 degrees or more apart, preferably about 105 degrees or more apart, more preferably about 125 degrees or more apart, even more preferably about 160 degrees or more apart, and most preferably about 175 degrees or more apart. The one or more circular segments may form an end piece. The one or more circular segments may include two 90 degree portions. For example, the circular segment may be generally square in shape or include a square shaped portion and circle around so that both ends face the same direction. The circular segment may be triangular in shape or include a triangular shaped portion. The circular segments may be tangent to one or more tangent segments, one or more oblique segments, or both. The circular segments may be part of the tangent portion, the circular portion, or preferably both.

The one or more circular portions may include one or more circular segments. The one or more circular portions may function to receive all or a portion of an endoscope. The one or more circular portions may be located opposite the tangent portion, connected to the tangent portion, or both. The one or more circular portions may be the larger side and/or end of the sheath when compared to the tangent portion. The one or more circular portions may be any portion with a radius, an arc length, or both. The one or more, circular portions may include one or more circular segments as discussed herein. The one or more circular portions may generally mirror the shape of the endoscope. The one or more circular portions may terminate at the tangent portions, at the tangent segments, oblique segments, oblique portions, or a combination thereof. The circular portion may have a length that is substantially equal to the length of the tangent portion. For example, the perimeter of the cross-section of the sheath may be equally divided between the circular portion and the tangent portion. The one or more circular portions may be connected to one or more oblique segments, one or more tangent segments, or both. The one or more oblique segments may be part of an oblique portion that may extend all or a portion of a length of the sheath.

An oblique portion may extend from a first end towards second end of the tube and/or sheath. The one or more oblique portions may terminate before the oblique portions reach a second end of the tube and/or sheath. The one or more oblique portions may function to create a planar portion (i.e., a oblique segment) along a perimeter of the sheath when the sheath is viewed in the cross section. As discussed herein oblique portion is three dimensional and oblique segment and/or line is two dimensional (i.e., a cross-section). The one or more oblique portions may function to laterally displace, radially displace, circumferentially displace, or a combination thereof the endoscope within the sheath. Preferably, the oblique portions do not extend from one end to the second end e.g., a distal end to a proximal end). More preferably, the oblique portions extend to one end of the sheath only. The oblique portions may terminate before the oblique portions reach one or both ends. The oblique portions may at least partially helically rotate as the oblique lines longitudinally extend along the length of the sheath. The oblique portions may partially or fully rotate about the sheath, partially or fully helically wrap the sheath, or both. The oblique portions may wrap about 5 degrees or more, about 10 degrees or more, about 15 degrees or more around the sheath. The oblique portions may wrap about 180 degrees or less, about 135 degrees or less, about 105 degrees or less, about 90 degrees or less, or even about 60 degrees or less of the sheath. If more than one oblique portion is present, one oblique portion may be straight and one oblique portion may extend at an angle. The one or more oblique portions may include two edges and one edge may extend parallel straight between the distal end and the proximal end and the second edge may extend at an angle relative to the first edge as the second edge extends from the distal end towards the proximal end. The oblique portions may be located at the distal end only, in a distal end region, or both. The one or more oblique portions may be located on opposing sides of the sheath. All or a portion of the oblique portion may be tangent to an endoscope, a circular portion of the tube, or both when viewed in the cross-section. The oblique portion when viewed in the cross section may have one or more tangent segments, tangent lines, or both. Two or more oblique portions may be located on each side so that two or more oblique segments are formed.

The oblique segments may function to create a part of the sheath that contacts the endoscope so that the endoscope is shifted to one side of the sheath. The oblique segments as discussed herein, unless otherwise stated, are discussed in the cross-section, but are a part of a larger line that extends partially or fully along a length of the sheath. The oblique segments may function to create a channel, a lumen, a conduit, a gap, or a combination thereof at one end of a sheath and be substantially free of a defined channel, lumen, conduit, a gap, or a combination thereof at a second end (i.e., formed from a non-circular portion). The oblique segments may function to shape the sheath so that the sheath has a non-circular shape, is oblong, oval, elliptical, egg shaped, obround, or a combination thereof. The oblique segments may gradually shorten in length so that as cross-sections are taken from the distal end towards the proximal end. The oblique segments may terminate before the proximal end so that a cross-section taken proximate to the proximal end will be free of oblique segments. The oblique segments may be generally planar, linear, straight, flat, be concave, be convex, or a combination thereof. The oblique segments may be tangent to the circular portions, the circular segments, the endoscope, or a combination thereof. The oblique segments may connect two circular segments together. The oblique segments may result in one end of the sheath being circular and one end of the sheath being non-circular (e.g., oblong).

A perimeter of the circular end and the non-circular end may be equal. A perimeter of the distal end and the proximal end may be equal. A cross-sectional length of the largest portion of the non-circular end may be the same as or greater than the cross sectional length of the largest portion of the circular end. The cross-sectional area of the circular end may be the same as the cross-sectional area of the non-circular end. The cross-sectional area of the distal end may be the same as the cross-sectional area of the proximal end. The area of the non-circular end may be greater than the area of the circular cross-sectional end. The area of the non-circular end may be sufficiently large so that a conduit, channel, lumen, or a combination thereof is created that may transfer irrigation fluid, suction, a functional device, or a combination thereof. The area of the non-circular end may function to transport Items moved into the sheath through the port.

The port may function to provide access into the tube of the sheath. The port may function to provide a fluid connection, a connection with one or more irrigation sources, a connection with one or more suction sources, one or more common lines, one or more delivery lines, or a combination, thereof. The port may form a fixed connection with one or more lines so that suction, irrigation fluid, or both may be provided through the port. The port may provide direct access to the inside of the tube. The port may be configured so that one or more functional elements (e.g., a cutting tool, a cauterizing tool, or both may gain access to the inside of the tube of the sheath, may extend out of the distal end of the sheath, or both. For example, the port may not be receive items that flow. The port may be part of a handpiece of the sheath. The port may be part of the tube, the hub, or both.

The hub may function to connect the sheath to the endoscope. The hub may function to seal the sheath to the endoscope. The hub may surround a portion of the endoscope. The hub may function to create a fluid seal with the endoscope so that irrigation fluid, suction, or both do not leak. The hub may receive a shoulder of the endoscope so that the shoulder and the hub form a fluidly sealed connection. The hub may have a circular cross section. The hub may taper as it extends towards the distal end of the sheath. The hub may be large enough to receive all or a portion of the endoscope. The hub may partially extend around the endoscope, fully extend around the endoscope, or a combination of both. The hub may have a thicker section that connects to the tube. The hub may be fastened to the tube. The hub may be connected to the tube by a mechanical fastener such as threads, a snap, a one way connection system, a series of ribs, or a combination thereof. The hub may connect to the tube by one or more adhesives. The hub may include a collar, an arm, or both that, receive all or a portion of the endoscope.

The collar may be an integral part of the hub. The collar may function to axially align, rotationally align, or both the endoscope and the sheath. The collar may form a majority of the hub (e.g., 50 percent or more, 60 percent or more, or 70 percent or more). The collar may function to prevent rotational movement. The collar may function to prevent axial movement. The collar may function to receive all or a portion of the endoscope. The collar may function to receive alight post of the endoscope. The collar may surround the light post. The collar may extend partially around the light post. The collar and/or a region proximate to the collar may include one or more spacers.

The one or more spacers may function to axially align the endoscope within the sheath. The one or more spacers may contact a shoulder of the endoscope and align the endoscope within the sheath. The spacer may contact an endoscope so that the endoscope is axially aligned within the tube. The one or more spacers may be optional. The spacer may be located proximate to one or more O-rings.

The one or more O-rings may function to form a seal between the sheath and a tube of the endoscope. The one or more O-rings may function to prevent fluid from traveling towards the proximal end of the endoscope. The one or more O-rings may function to create a seal. The one or more O-rings may be located within the hub, proximate to a collar of the hub, or both. The one or more O-rings may be made of any material that forms a seal. The one or more O-rings may create a circumferential seal, a thrust seal, or both. The one or more O-rings may be axially compressed, radially compressed, radially expanded, or a combination thereof. The one or more O-rings may include one or more through holes. The one or more O-rings may elastically deform. The one or more O-rings may be made of an elastomer, include elastic, include rubber, include a deformable material, include a deformation region, or a combination thereof. The one or more O-rings may be located proximate to a locking ring.

The one or more locking rings may lock the O-ring to the sheath, the endoscope, or both. The one or more locking rings may function to lock two or more components together. The one or more locking rings may include a through hole so that the endoscope extends through the tube and the locking ring.

A through hole may extend from a proximal end to a distal end of the sheath. A through hole may be sufficiently large so that the endoscope and fluid (e.g., irrigation fluid, suction, or both) may pass from the distal end to the proximal end of the sheath. The tube may include one or more through holes in the sheath. The through hole in the tube may open directly to a point of interest, an internal location of a patient, or both. The through hole may include one or more flow directors.

FIG. 1A illustrates a top view of sheath 90 for use with an endoscope cleaner system (not shown). The sheath 90 includes a distal end 92 and a proximal end 94. A tube 96 and hub 98 extend between the distal end 92 and the proximal end 94. The hub 98 includes a port 106 for receiving suction, an irrigation fluid, or both. The hub 98 as shown has a collar 100 that includes an optional socket 102 for receiving a light post 72 (not shown) of a corresponding device (not shown) and the socket 102 includes an undercut 104 for forming a connection with the corresponding device.

Figure 1B:
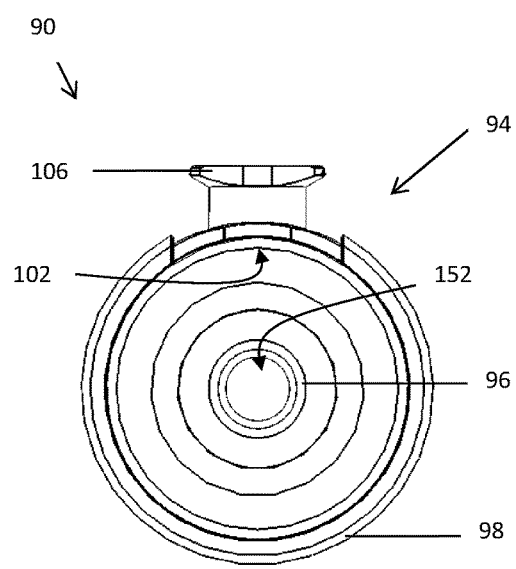
FIG. 1B illustrates a proximal end view of an endoscope sheath of FIG. 1A.

FIG. 1B illustrates an end view of the sheath 90 from the proximal end 94. The port 106 is shown extending from the hub 98 and a through hole 152 is shown extending through the tube 96 and hub 98. The socket 102 is illustrated extending through the hub 98 towards the port 106.

Figure 1C:
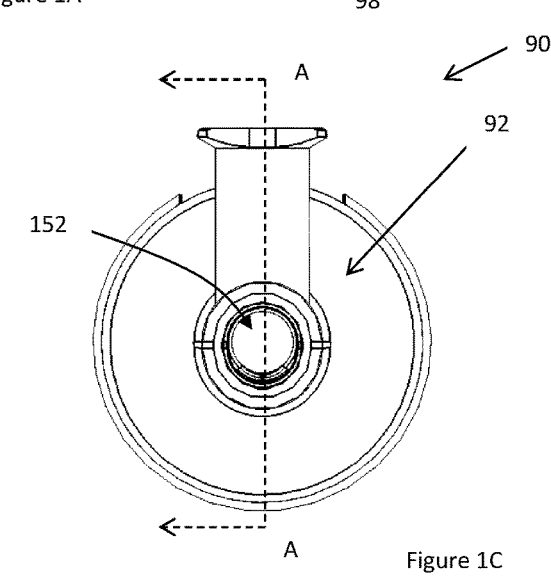
FIG. 1C illustrates a distal end view of an endoscope sheath of FIG. 1A.

FIG. 1C illustrates a view of the sheath 90 from the distal end 92. A through hole 152 is shown extending through the sheath 90.

Figure 2:
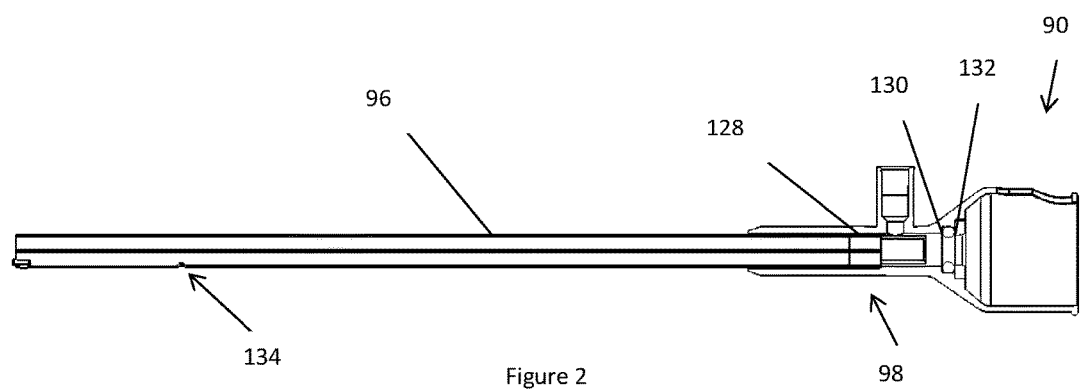
FIG. 2 illustrates a cross sectional view of FIG. IC along lines A-A.

FIG. 2 illustrates a cross sectional view of the sheath 90 of FIG. 1A cut along lines A-A of FIG. 1C. The sheath 90 includes a tube 96 connected to a hub 98. The hub 98 includes a spacer 128 between an end of the tube 96 and a mating surface of the hub 98. An O-ring 130 is located in the hub proximate to a locking ring 132 for creating connection between the hub 98 and an endoscope (not shown). The tube 96 includes a dimple 134 along the longitudinal axis of the tube 90.

Figure 3A:
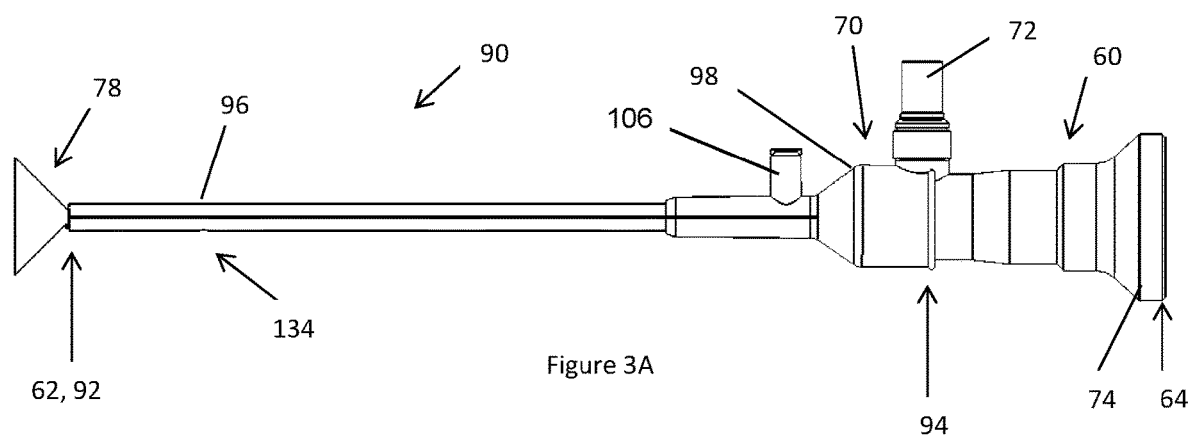
FIG. 3A illustrates a side view of an endoscope inserted in the endoscope sheath of FIG. 1A.

FIG. 3A illustrates an endoscope 60 extending into a sheath 90. The endoscope 60 includes a proximal end 64 including a visual port 74. The visual port 74 allows a user to view locations of interest located within the viewing cone 78 at the distal end 62 of the endoscope 60. The endoscope 60 includes a distal end 62 that extends to a distal end 92 of a sheath 90. The tube 96 of the sheath 90 includes a dimple 134 along its longitudinal axis that locates the endoscope 80 within the sheath 90. The sheath 90 includes a tube 96 extending from a distal end 92 to a hub 98. The hub 98 includes a port 106 for receiving suction, an irrigation fluid, or both. The hub 98 terminates at a proximal end 94 that receives a shoulder 70 and a light post 72 of the endoscope 60.

Figure 3B:
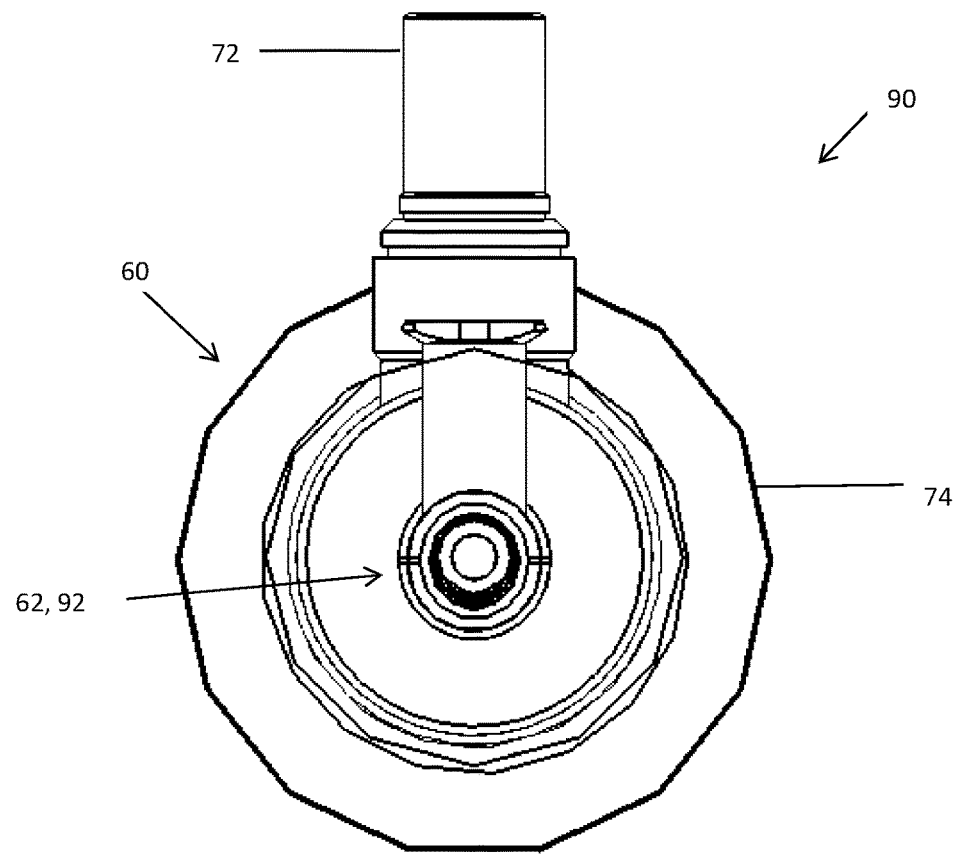
FIG. 3B illustrates a distal end view of FIG. 3A.

FIG. 3B illustrates an end view of the sheath 90 and endoscope 66 from a distal end 62, 92 respectively. The visual port 74 and light post 72 of the endoscope 60 extend outward from the endoscope 60.

Figure 4A:
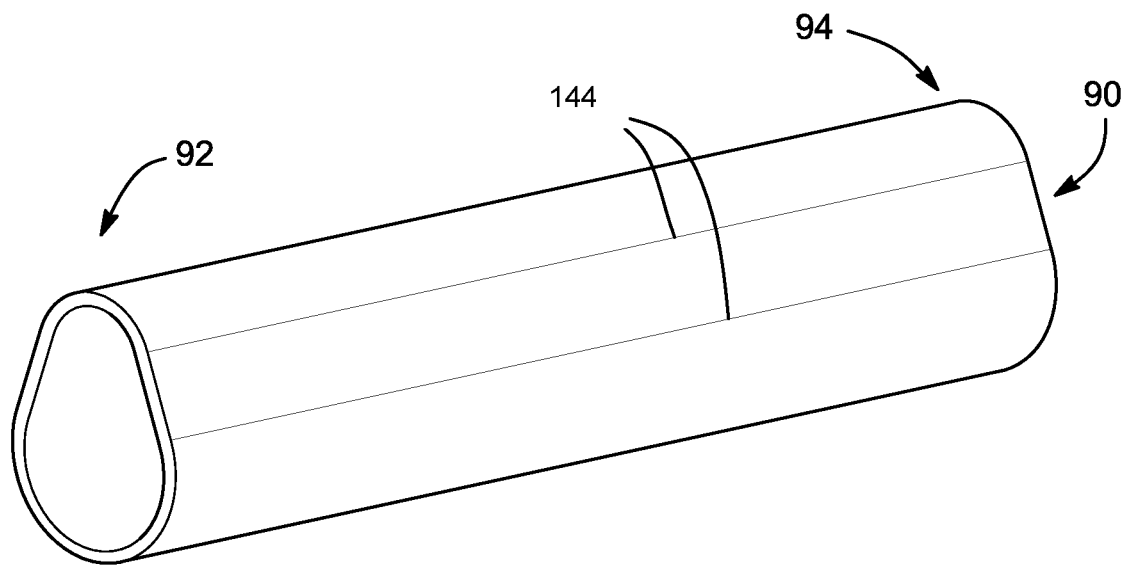
FIG. 4A illustrates a side view of a sheath having a non-circular perimeter.

FIG. 4A illustrates a perspective view of a sheath 90 including a tangent portion 144 that extend from the distal end 92 to the proximal end 94 so that a non-circular perimeter is formed along the longitudinal axis of the sheath 90.

Figure 4B:
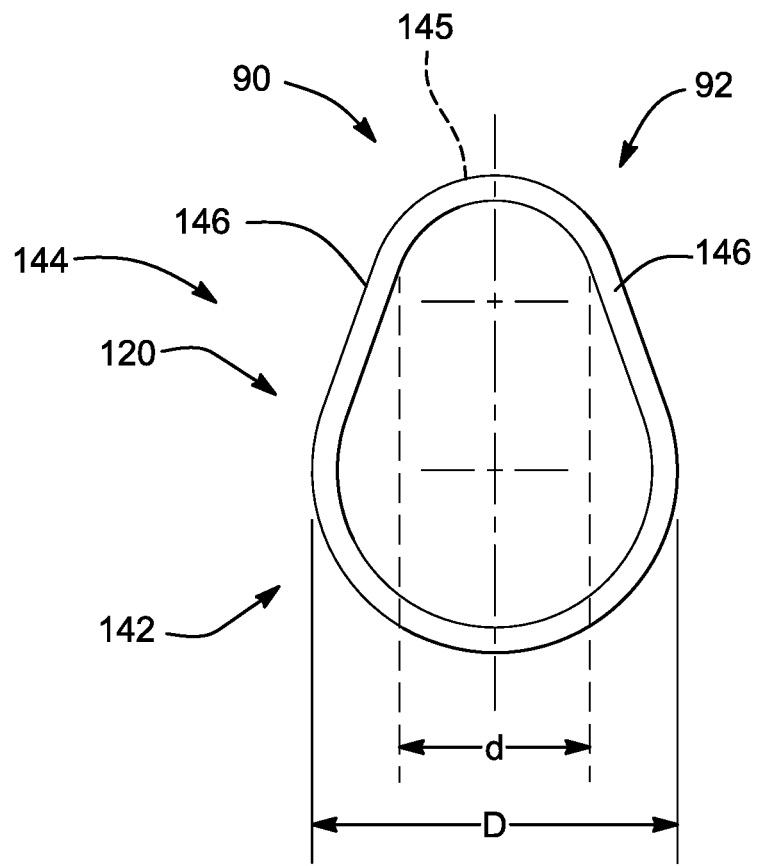
FIG. 4B illustrates a distal end view of the sheath of FIG. 4A.

FIG. 4B illustrates a distal end 92 view of the sheath 90. The distal end 92 of the sheath 90 has an oblong opening 120. The oblong opening 120 includes a circular portion 142 and a tangent portion 144. The tangent portion 144 includes two tangent segments 146 that are linear and a circular segment 145. The circular portion 142 and the tangent portion 144 are connected by the tangent segments 146. As illustrated, the circular portion 142 includes a diameter (D) and the tangent portion 144 includes a diameter (d) which is less than the diameter (D).

FIG. 5A illustrates a perspective view of a sheath 90 having oblique portions 182 that extend from the distal end 92 towards the proximal end 94 but the oblique portions 182 do not extend to the proximal end 94. The oblique portions 182 as illustrated partially helically wrap the sheath 90 as the oblique portions 182 extend from the distal end 92 to the proximal end 94 so that opposing edges of the oblique portions 182 converge and terminate.

FIG. 5B illustrates an end view of the sheath 90 from the distal end 92. The distal end 92 of the sheath 90 has an oblong shaped opening 120. The oblong opening 120 includes an oblique portion 182 having oblique segments 184 that are generally linear and connect the oblique portion 182 to a circular portion 142. The oblique portion 182 has oblique segments 184 that are also tangent segments 146, which are tangent to both the circular segment 145 of the circular portion 142 and the circular segment of the oblique portion 182.

FIG. 5C illustrates an end view of the sheath 90 from the proximal end 94. The proximal end is generally circular and is free of the oblique segments. The distal end 92 and the proximal end 94 (shown in FIGS. 5A and 5B) have a perimeter that are substantially equal.

FIG. 6A illustrates a perspective view of a tube 96 of the sheath 90. The tube 96 is oblong shaped 120 (i.e., obround) including two circular portions 142 that are connected by two tangent portions 144.

FIG. 6B illustrates an end view of the sheath 90 of FIG. 6A. The sheath 90 has an oblong shape (i.e., obround) with two opposing circular segments 145 that are connected together by tangent segments 146 when shown in the end view (i.e., a cross-sectional view). The two opposing circular segments 145 are cradles that form the obround shape.

FIG. 6C illustrates an end view of a sheath 90, including two opposing circular segments 145 that are connected together by tangent lines 147. One of the circular segments 145 includes a dimple 134 that offsets the endoscope 60 within the sheath 90. The endoscope 60 contacts the tangent lines 147 at a contact location 223, which is also a location where the tangents segments 146 are tangent to the endoscope 60. Each of the tangent segments 146 are also tangent with each of the circular segments 145.

FIG. 7 illustrates a sheath 90 including a tangent segment 140 connected to a circular portion 142. An outer wall of the endoscope 60 is in contact with the circular portion 142 along it perimeter and the endoscope 60 is in contact with tangent portions 146 of the circular portion 142 at contact locations 223. The vertical tangent portions 146 are tangent to the endoscope 60 and are contiguous with the circular portion 142.

FIG. 8 illustrates a sheath 90 including four tangent segments 146 forming a generally square perimeter. The endoscope 60 is in contact at a point with each of the tangent lines 147 forming gaps 222 past the endoscope 60.

Figure 9A:
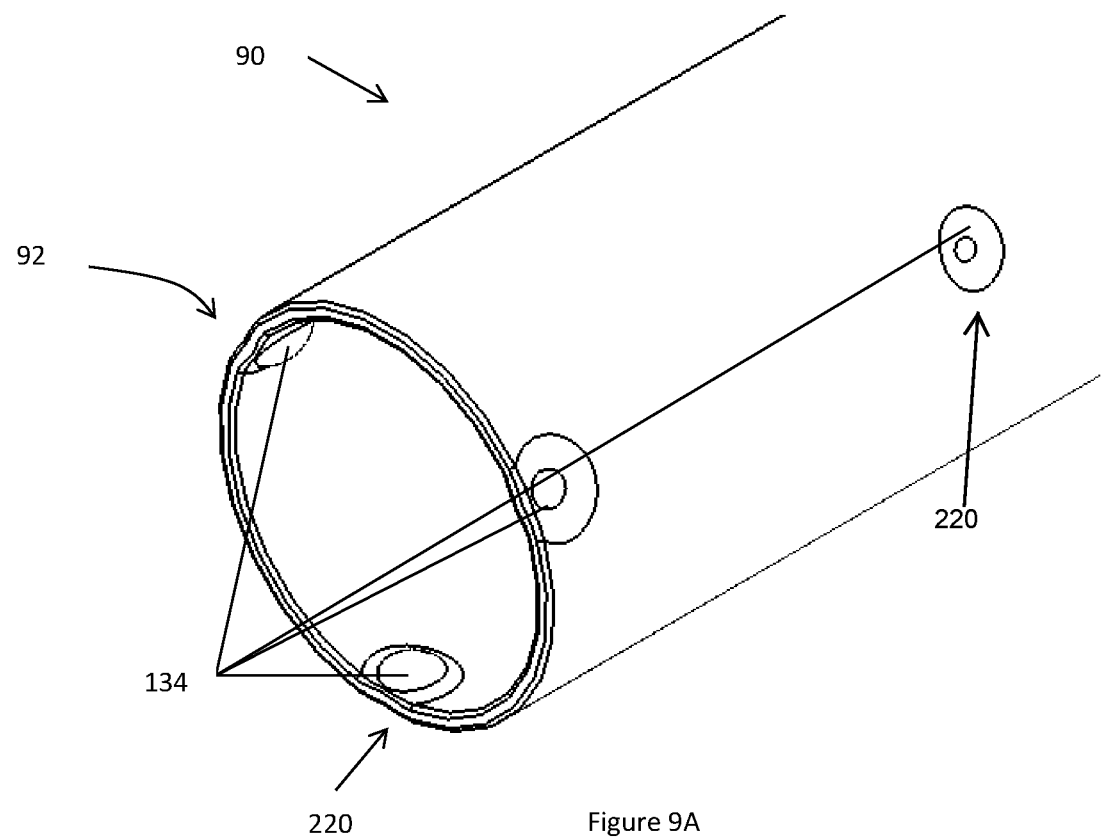
FIG. 9A illustrates a perspective view of a sheath including a plurality of positioning devices that are aligned.

FIG. 9A illustrates a perspective view of a sheath 90. The sheath includes a plurality of positioning devices 220. The positioning devices 220 are configures as dimples 134 with a set of three dimples located at the distal end 92 and a set of three dimples 134 at a location proximal of the distal end 92.

Figure 9B:
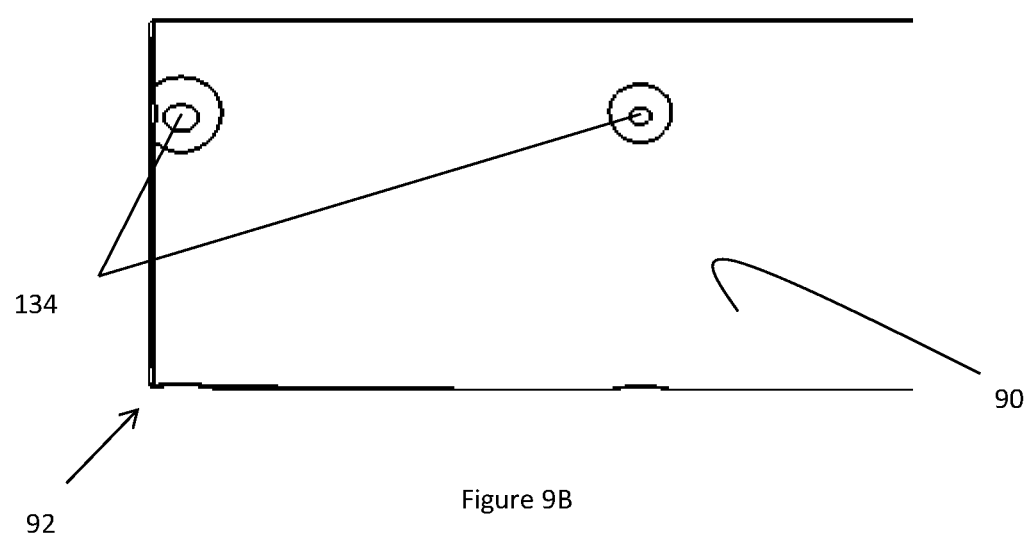
FIG. 9B illustrates a side view of the sheath of FIG. 9A.

FIG. 9B illustrates a side view of the sheath 90 of FIG. 9A. The sheath 90 has a first set of dimples 134 at the distal end and a second set of dimples 134 located on the proximal side of the flat set so that the endoscope (not shown) forms an annular gap along its length.

Figure 9C:
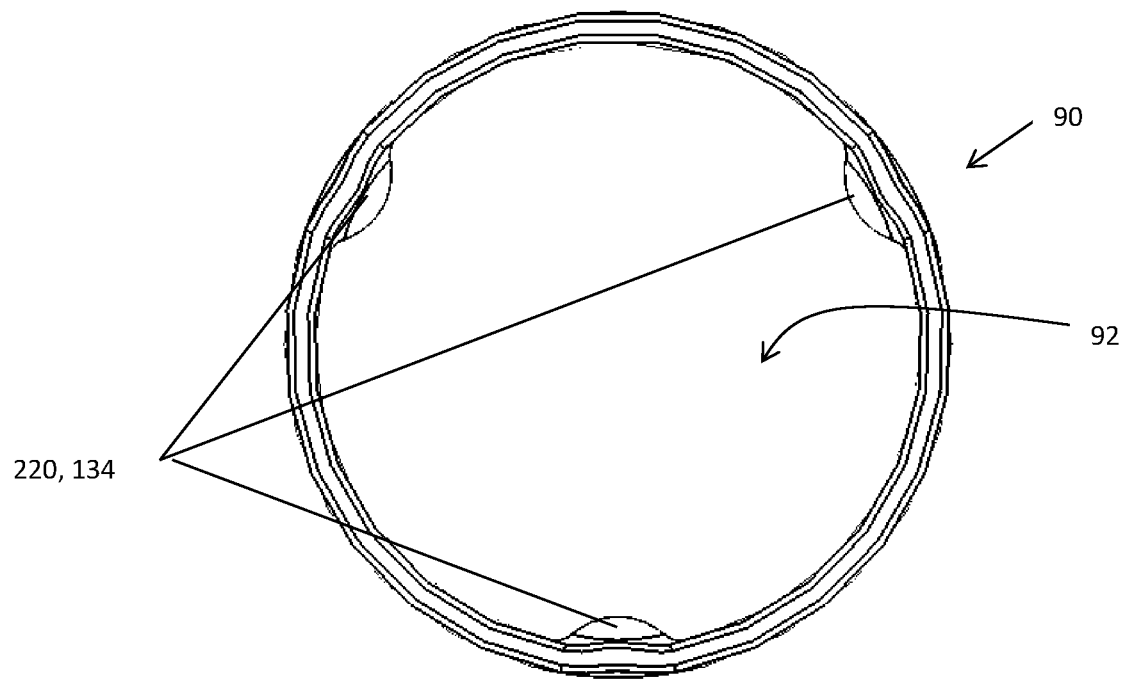
FIG. 9C illustrates an end view of the sheath of FIG. 9A

FIG. 9C illustrates an end view of the distal end 92 of the sheath 90 of FIG. 9A. The sheath 90 includes a three positioning devices 220 that are configured as dimples 134 equally spaced so that when an endoscope (not shown, placed in the sheath 90 an equally sized annular gap is created around the endoscope.

Figure 10A:
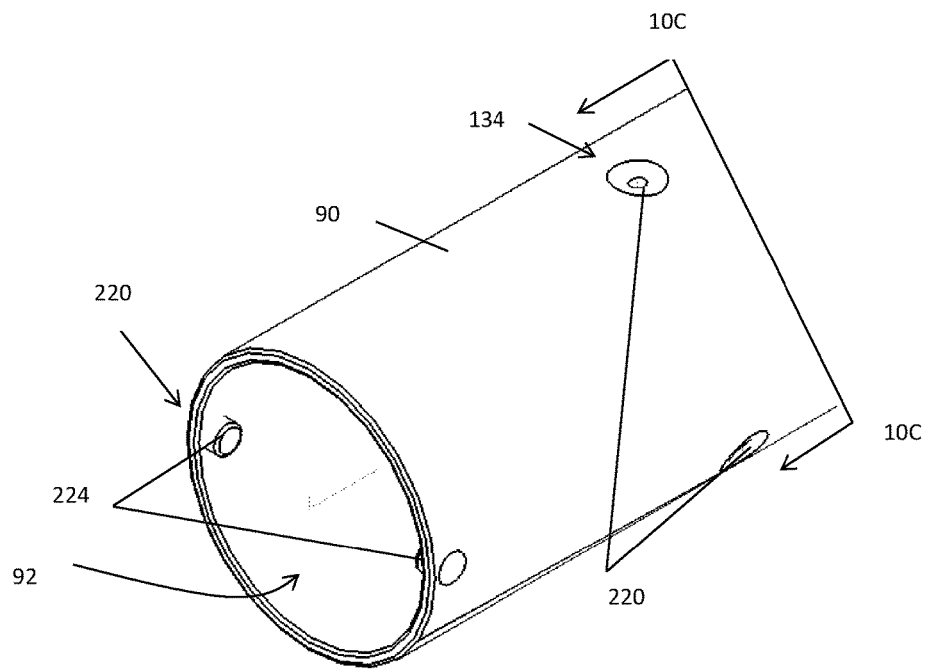
FIG. 10A illustrates a perspective view of a sheath having a plurality pf positioning devices that are off set.

FIG. 10A illustrates a perspective view of a sheath 90 having two sets of positioning devices 220. The first set of positioning devices 220 is located at the distal end 92 and is a set of pins 224 that create a distal end stop for an endoscope (not shown). The second, set of positioning devices 220 which are located towards the proximal end relative to the first set of positioning devices 220 are configures as a plurality of dimples 134 that are located around the inside of the sheath 90.

Figure 10B:
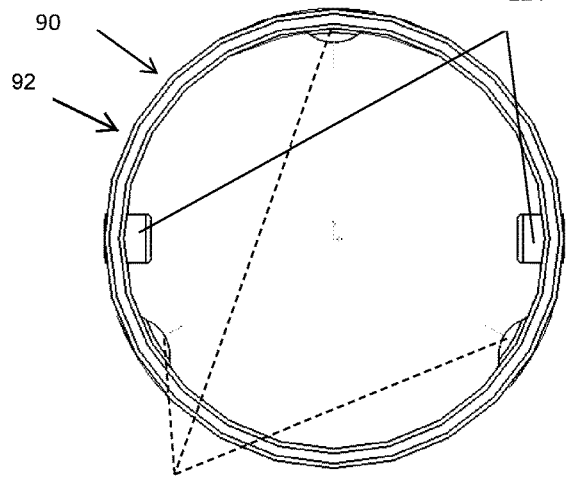
FIG. 10B illustrates an end view of the sheath of FIG. 10A.

FIG. 10B illustrates the sheath 90 from the distal end 92. The pins 224 are offset from the dimples 134 and the dimples 134 are equally spaced apart around the sheath 90.

Figure 10C:
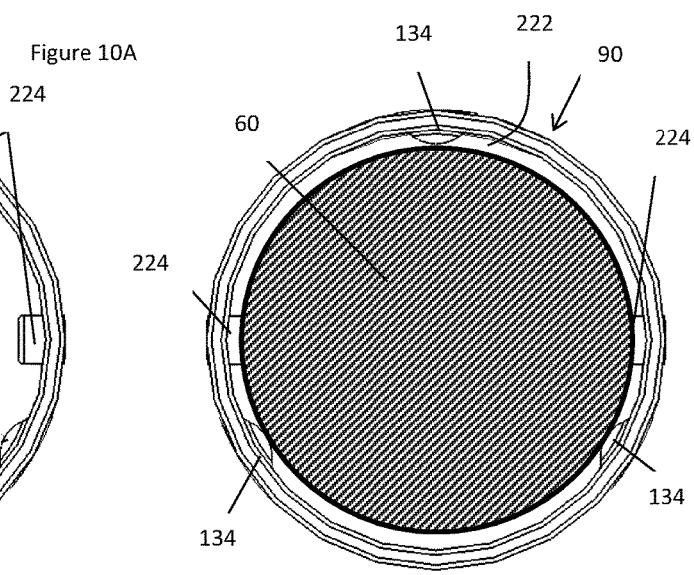
FIG. 10C illustrates a view of the proximal end side of the endoscope of FIG. 10A.

FIG. 10C illustrates a view of the sheath 90 from a proximal end looking along line 10C-10C towards the distal end. The sheath 90 includes an endoscope 60 that is in contact with the pins 224 located on opposing sides of the sheath 90 so that the endoscope 60 is prevented from moving axially towards the distal end. The sheath 90 includes three dimples 134 that are spaced apart forming a gap 222 that is annular round the outside of the endoscope 60.

Figure 11C:
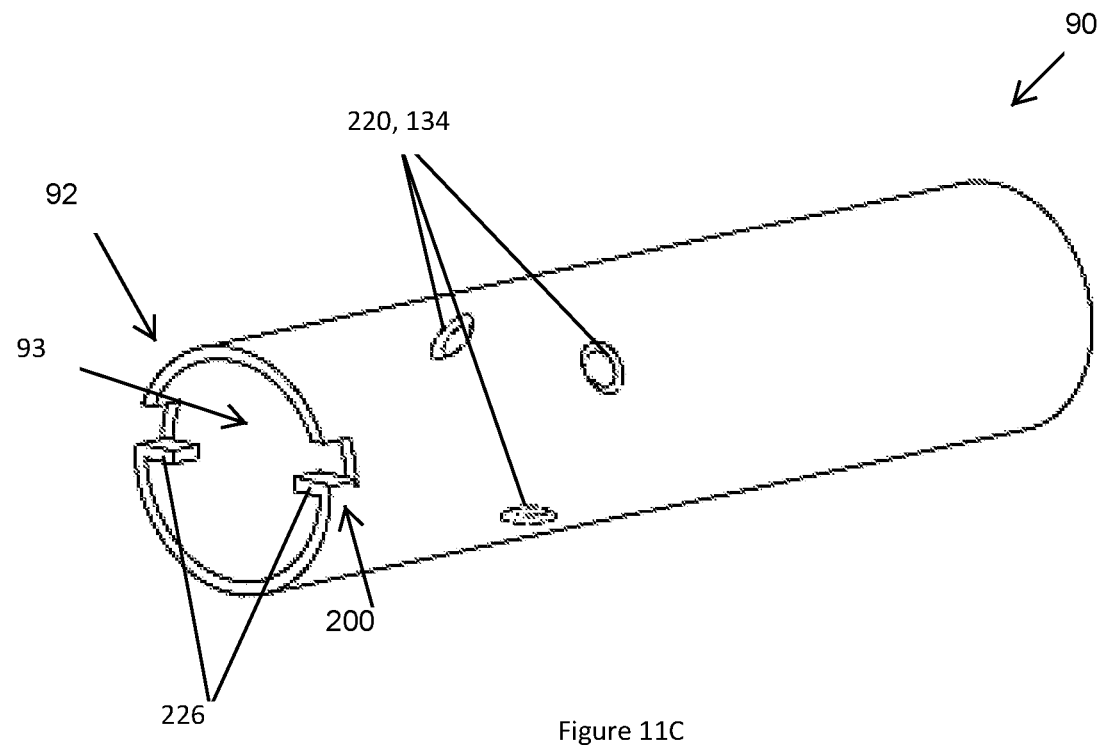
FIG. 11C illustrates a perspective view of a sheath having two different positioning devices.
Figure 11A:
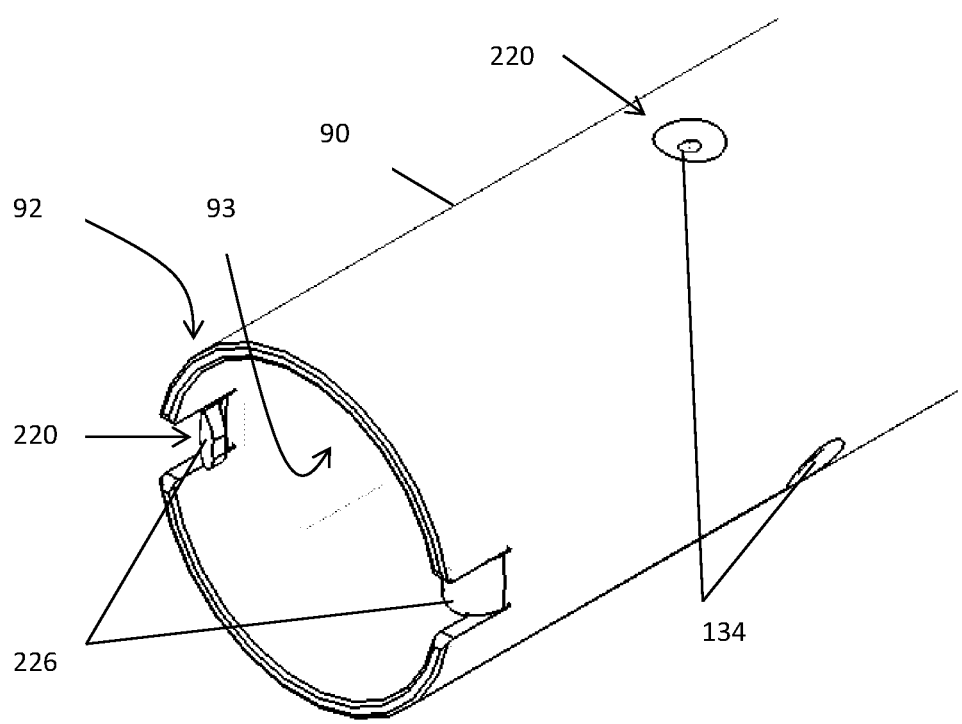
FIG. 11A illustrates a perspective view of a sheath having a plurality of two different positioning devices that are off set.

FIG. 11A illustrates a perspective view of a sheath 90 having an opening 93 at the end of the sheath 90 (i.e., a 0 degree sheath). The sheath 90 includes two sets of positioning devices 220. The first set of positioning devices 220 are crimps 226 that are located at the distal end 92. The second set of positioning devices 220 are dimples 134 that are located proximal of the distal end 92.

Figure 11B:
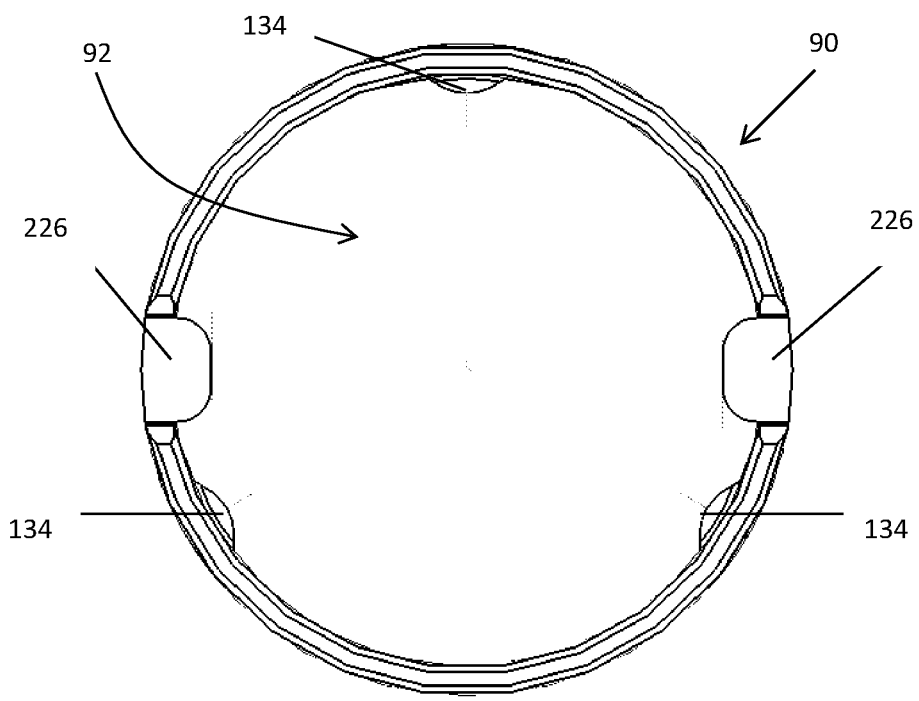
FIG. 11B illustrates an end view of the sheath of FIG. 11A.

FIG. 11B illustrates a view of the distal end 92 of the sheath 90. The sheath 90 includes a pair of opposing crimps 226 that prevent an endoscope (not shown) from extending out the distal end of the sheath 90. The sheath 90 also includes dimples 134 spaced around the sheath 90 and rotationally offset from the crimps 226 so that the endoscope (not shown) is positioned within the sheath 90.

FIG. 11C illustrates a perspective view of a sheath 90 including two sets of positioning devices 220. A first set of positioning devices 220 are configured as crimps 226 at the distal end 92 with the crimps 226 extending inward towards each other within the opening 93 of the sheath 90. A second set of positioning devices 220 are located proximal of the first set of positioning devices 220 and the second set are configured as dimples 134 for that are equally spaced apart around a circumference of the cylindrical sheath 90.

Figure 12A:
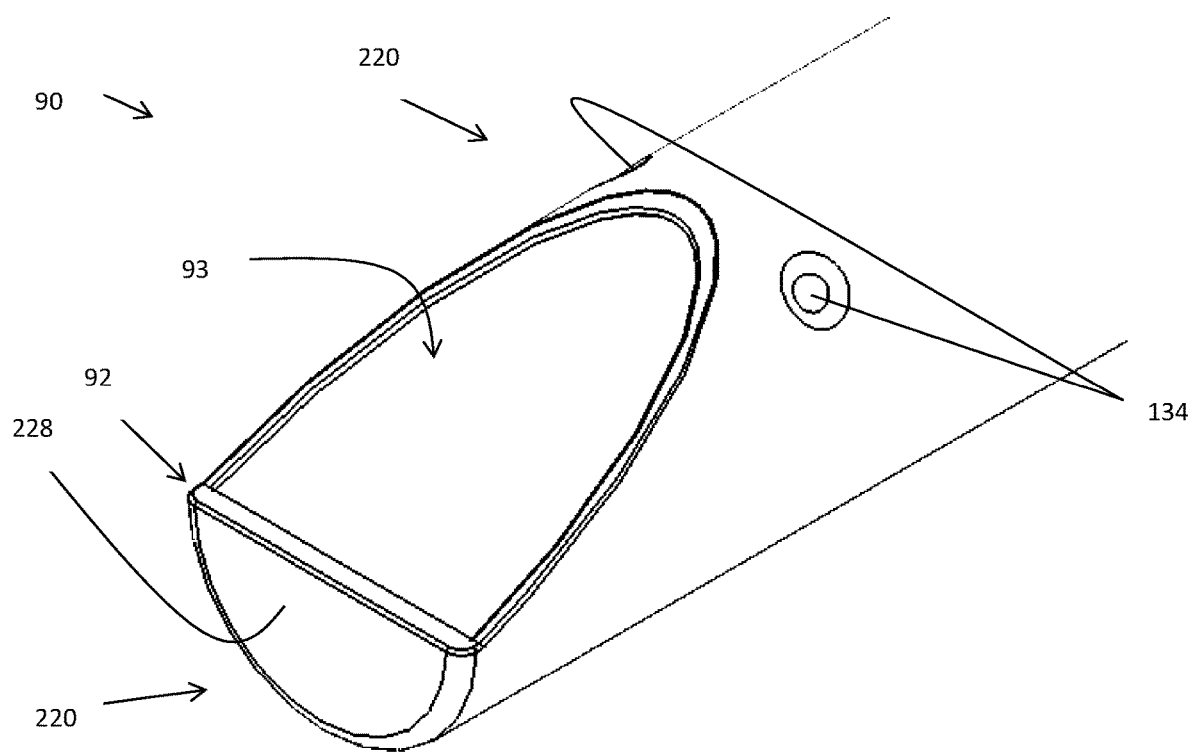
FIG. 12A illustrates a perspective view of an angled sheath eying a plurality of positioning devices.

FIG. 12A illustrates an angled sheath 90 having an opening 93 on the side of the sheath 90 (i.e., a 70 degree sheath). The angled sheath 90 includes a positioning device 220 that is an end stop 228 and prevents movement of an endoscope (not shown) within the sheath towards the distal end 92. The angled sheath 90 further includes positioning devices 220 that are configured as dimples 134. The dimples 134 as shown are located on a single side of the sheath 90 and locate the endoscope (not shown) so that the endoscope is positioned against one side of the sheath 90 preventing the flow of fluid through a portion of the sheath 90 and moving the fluid so that all of the fluid moves through a portion of the sheath 90 positioned relative to the dimples 134.

Figure 12B:
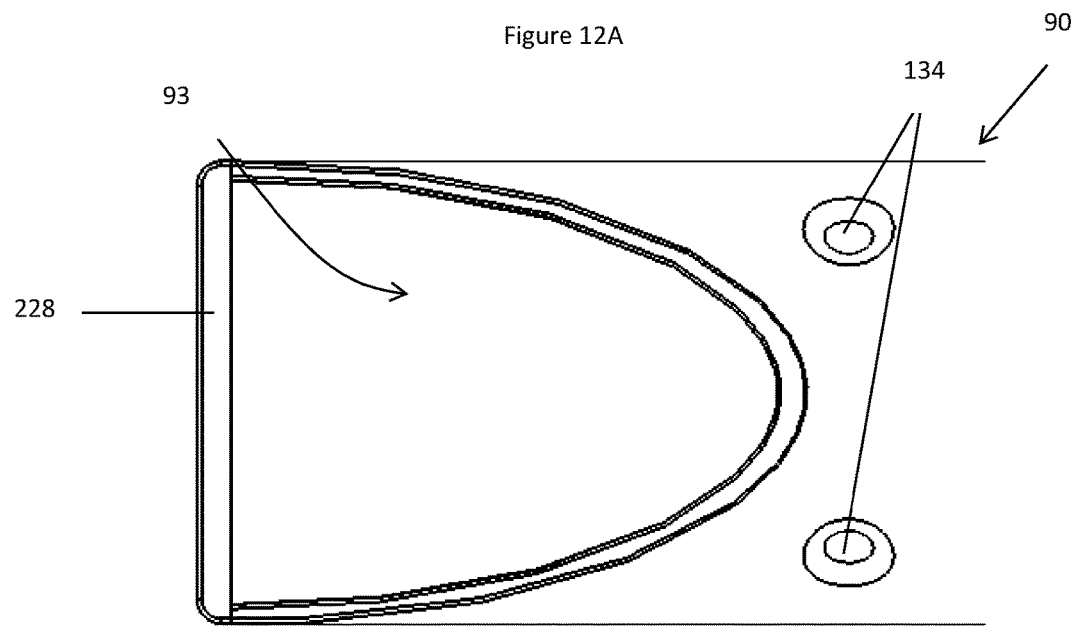
FIG. 12B illustrates a top view of the sheath of FIG. 12A.

FIG. 12B illustrates a top view of a sheath 90. The opening 93 is in the side of the sheath 90 and terminates at an end stop 228 that prevents an endoscope (not shown) from moving axially towards a distal end. A pair of dimples 134 are spaced apart and located on the side of the sheath 90 relative to the opening 93 so that fluid during an application cycle is moved across the endoscope cleaning its lens, imaging device, or both.

Figure 12C:
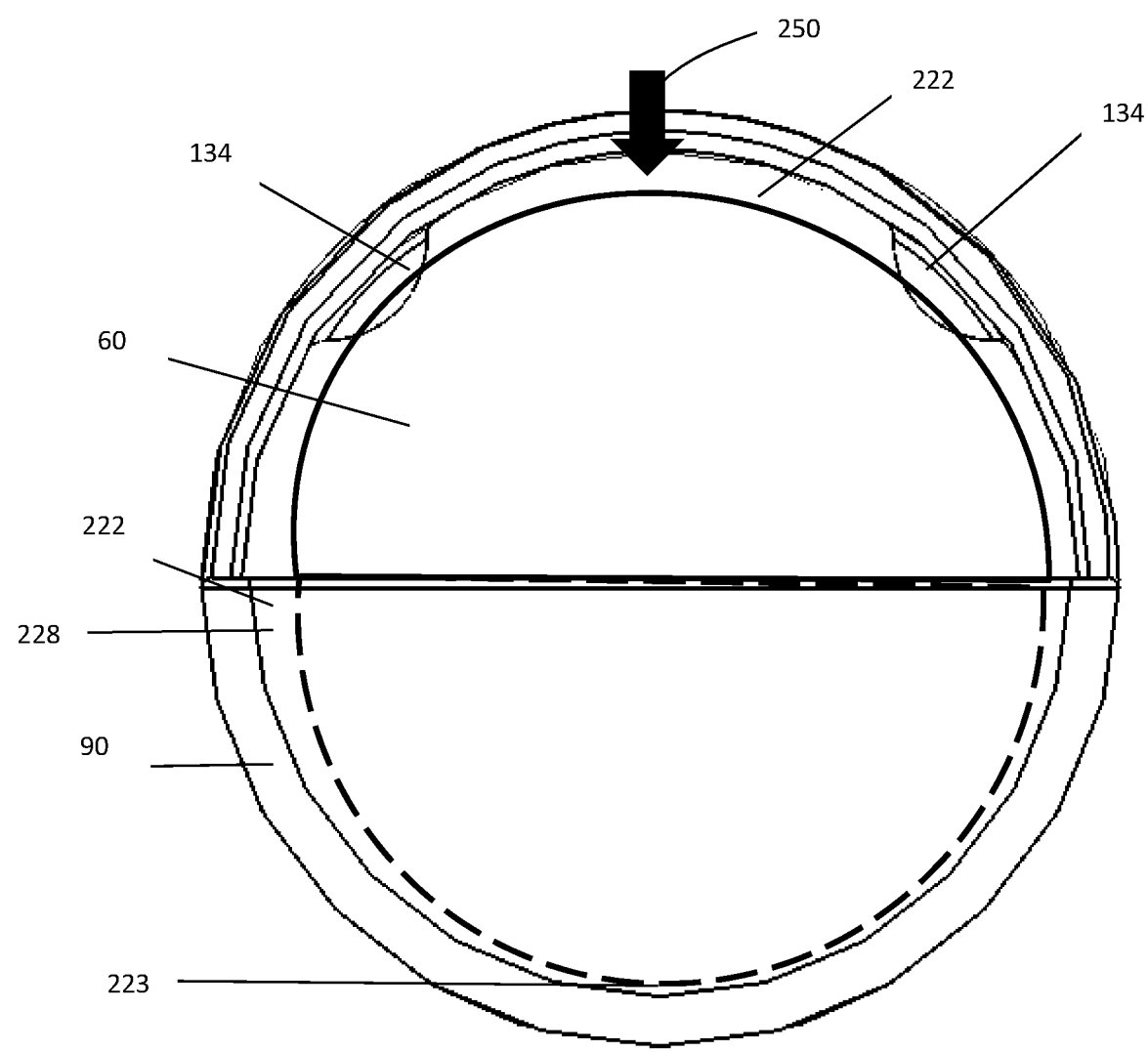
FIG. 12C illustrates an end view of the sheath of FIG. 12A.

FIG. 12C illustrates an end view of the sheath 90 of FIG. 12C including an endoscope 60 extending through the sheath 90. The endoscope 60 is in contact with an end stop 228, visible through a gap 222 and is shown in transparent, so that the contact location 223 between the endoscope 60 and the sheath 90 are in contact. The dimples 134 moves the endoscope 60 in the direction 250 so that a gap 222 is created between the endoscope 60 and a sheath 90 on a top side of the sheath 90 so that fluid can flow through gap 22, and a contact location 223 is formed between the endoscope 60 and the sheath 90 so that fluid flow is prevented.

Figure 13:
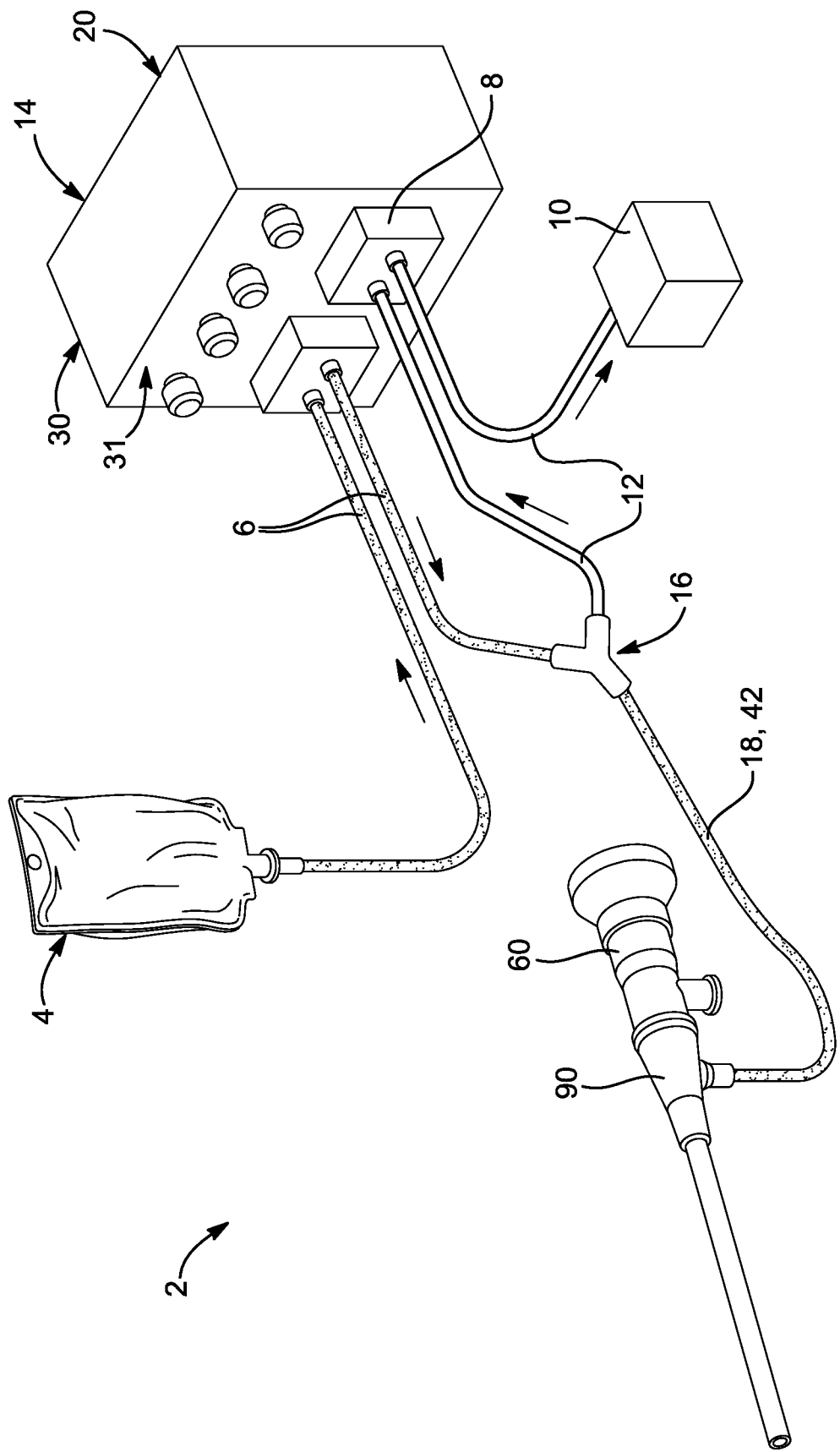
FIG. 13 illustrates a system including the sheath of the teachings herein.

FIG. 13 illustrates an endoscope cleaning system 2. The endoscope cleaning system 2 includes an irrigation source 4 connected to an irrigation line 6 that is connected to a control module 30 that includes a pump 14 for controlling flow of irrigation fluid between the irrigation source 4 and a sheath 90. The control module 30 includes a power source 20 and a controller and/or microprocessor (not shown) that is in communication with a user interface 31 for controlling the control module 30. The system 2 includes a suction source 10 that is connected to the control module 30. The control module 30 includes a valve 8 in the suction line that is connected to a sheath 90, which receives a portion, of an endoscope. The valve 8 for controls suction between the suction source 10 and the sheath 90 so that suction may be turned off during all or portion of the application cycle of the irrigation fluid. The irrigation line 6 and the suction line 12 are connected together at a common fitting 16 that connects the irrigation line 6 and the suction line 12 to a common line 18/delivery line 42 for supplying a fluid or suction to the sheath 90 for cleaning an endoscope (not shown).

Figure 14:
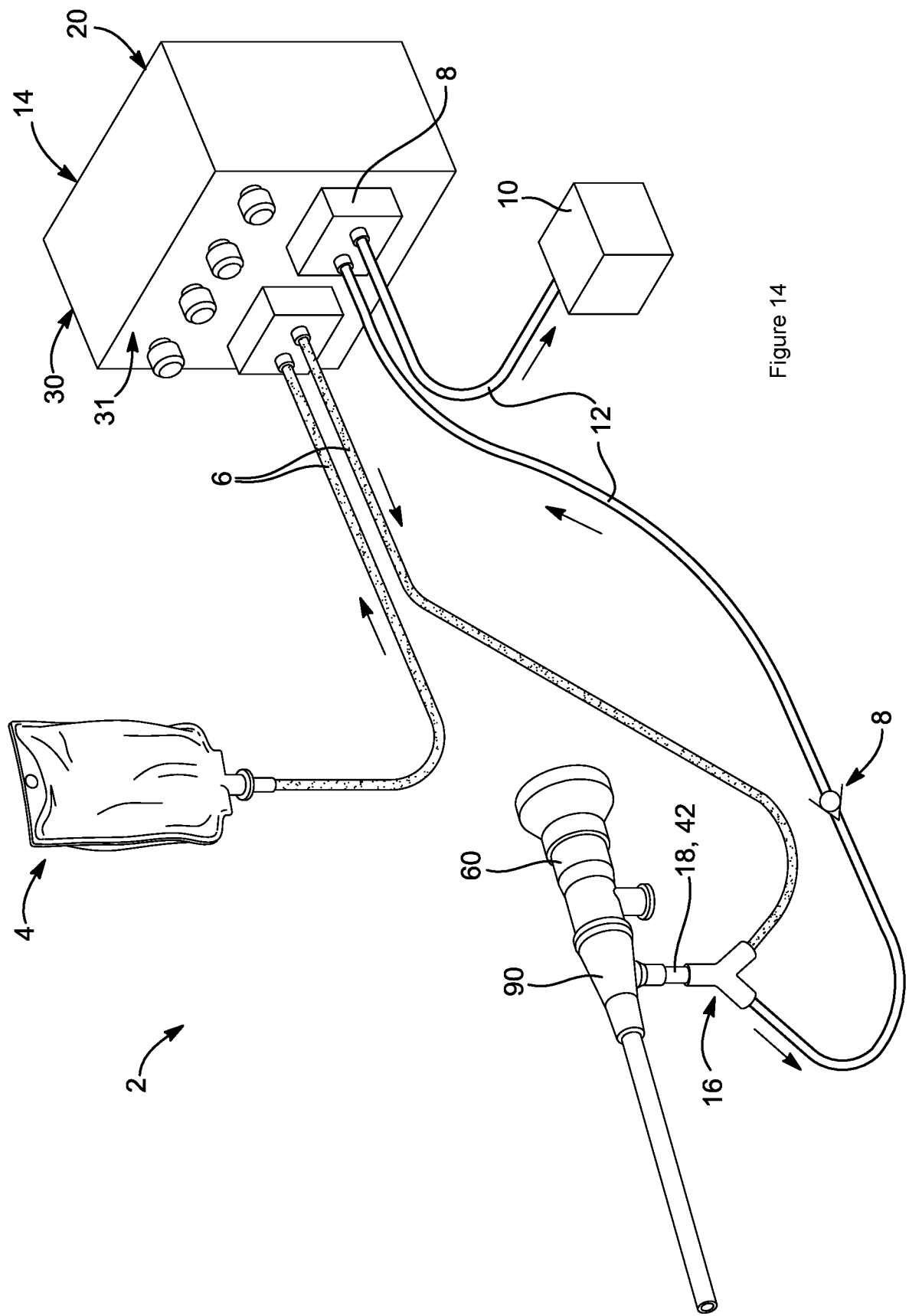
FIG. 14 illustrates another system including the sheath of the teachings herein.

FIG. 14 illustrates a control module 30 that includes a pump 14, a power source 20, a user interface 31, and one or more valves 8. The irrigation source 4 is gravity fed into the pump 14 and then the pump 14 sends fluid through the irrigation line 6 to the sheath 90 so that the sheath 90 washes the endoscope 60. The suction source 10 is connected to a valve 8 of the control module 30 that controls suction being drawn through the suction lines 12. Both the irrigation lines 6 and the suction lines 12 are connected to a common fitting 16 and a single common line 18/delivery line 42 extend from the common fitting 16 to the sheath 90. The suction line 12 may include a valve 8 that is a passive check valve to prevent irrigation fluid being forced into the suction line.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps. By use of the term "may" herein, it is intended that any described attributes that "may" be included are optional.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

We claim:

1. An endoscope sheath comprising:
    a tubular member extending from a proximal-most end to a distal-most end along a longitudinal axis and including a tubular wall; and
    a positioning device located on the tubular member;
    wherein the endoscope sheath is configured to receive a portion of an endoscope;
    wherein the positioning device is a crimp that is configured to prevent distal movement of the portion of the endoscope relative to the tubular member;
    wherein the crimp comprises first and second cuts formed in the distal-most end of the tubular member that extend through the tubular wall in a proximal direction; and
    wherein the crimp is folded in a direction of the longitudinal axis such that the crimp is proximally offset from the distal-most end of the tubular member.

2. The endoscope sheath of claim 1, wherein the endoscope sheath extends along a longitudinal axis, and the crimp is hinged generally orthogonal to the longitudinal axis.

3. The endoscope sheath of claim 1, wherein the crimp is a portion of the endoscope sheath that is folded.

4. The endoscope sheath of claim 3, wherein the crimp is a distal-most portion of the tubular member that is cut and folded in a direction of a longitudinal axis of the tubular member.

5. The endoscope sheath of claim 2, wherein the endoscope sheath comprises a second crimp that is hinged generally orthogonal to the longitudinal axis.

6. The endoscope sheath of claim 5, wherein the second crimp opposes the crimp.

7. The endoscope sheath of claim 6, wherein the crimp and the second crimp are portions of the tubular member that are cut and folded.

8. The endoscope sheath of claim 7, wherein the crimp points towards the second crimp.

9. The endoscope sheath of claim 5, wherein the second crimp comprises third and fourth cuts formed in the distal-most end of the tubular member.

10. The endoscope sheath of claim 9, wherein the second crimp is folded towards the opposing crimp.

11. The endoscope sheath of claim 9, wherein an inner portion of the endoscope sheath comprises one or more dimples that are configured to move the endoscope into contact with an inner wall of the endoscope sheath.

12. The endoscope sheath of claim 1, wherein the tubular member extends along a longitudinal axis, and one or both of the cuts are generally parallel to the longitudinal axis.

13. An endoscope sheath comprising:
    a tubular member extending from a proximal-most end to a distal-most end along a longitudinal axis and including a tubular wall; and
    a positioning device;
    wherein the tubular member is configured to receive a portion of an endoscope; and
    wherein the positioning device comprises a crimp that is configured to prevent distal movement of the portion of the endoscope relative to the tubular member,
    wherein the crimp is a portion of the tubular member that is folded, and
    wherein the crimp is defined by first and second cuts in the tubular member that begin at a distal-most end of the tubular member and extend through the tubular wall in a direction towards a proximal end of the tubular member; and
    wherein the crimp is folded in a direction of the longitudinal axis such that the crimp is proximally offset from the distal-most end of the tubular member.

14. The endoscope sheath of claim 13, wherein the positioning device comprises a second crimp that is a portion of the tubular member that is folded, and
    wherein the crimp is folded in a direction of the second crimp.

15. The endoscope sheath of claim 14, wherein the endoscope sheath extends along a longitudinal axis, and the crimp and the second crimp are each hinged generally orthogonal to the longitudinal axis.

16. The endoscope sheath of claim 11, wherein the two or more dimples are indentations formed in an outer surface of the endoscope sheath.

17. The endoscope sheath of claim 11, wherein the one or more dimples are configured to position the endoscope within the endoscope sheath so that a conduit is created so that irrigation fluid can be moved over a viewing lens of the endoscope.

\* \* \* \* \*